US012077820B2

(12) United States Patent
Poirier et al.

(10) Patent No.: US 12,077,820 B2
(45) Date of Patent: Sep. 3, 2024

(54) BIOMARKERS FOR ASSESSING THE RESPONSE STATUS FOR TREATMENT OF INFLAMMATORY CONDITION OR DISEASE AFFECTING THE DIGESTIVE TRACT SUCH AS INFLAMMATORY BOWEL DISEASE IN HUMAN PATIENTS

(71) Applicants: OSE IMMUNOTHERAPEUTICS, Nantes (FR); CENTRE HOSPITALIER UNIVERSITAIRE DE NANTES, Nantes (FR)

(72) Inventors: Nicolas Poirier, Treillieres (FR); Richard Danger, Reze (FR)

(73) Assignees: OSE IMMUNOTHERAPEUTICS, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 656 days.

(21) Appl. No.: 16/636,162

(22) PCT Filed: Aug. 3, 2018

(86) PCT No.: PCT/EP2018/071206
§ 371 (c)(1),
(2) Date: Feb. 3, 2020

(87) PCT Pub. No.: WO2019/025624
PCT Pub. Date: Feb. 7, 2019

(65) Prior Publication Data
US 2020/0181706 A1 Jun. 11, 2020

(30) Foreign Application Priority Data
Aug. 3, 2017 (EP) .................................... 17306039

(51) Int. Cl.
| | |
|---|---|
| C12Q 1/68 | (2018.01) |
| C07K 16/24 | (2006.01) |
| C07K 16/28 | (2006.01) |
| C12P 19/34 | (2006.01) |
| C12Q 1/6883 | (2018.01) |
| G01N 33/543 | (2006.01) |

(52) U.S. Cl.
CPC .......... C12Q 1/6883 (2013.01); C07K 16/241 (2013.01); C07K 16/2839 (2013.01); C12Q 2600/106 (2013.01); C12Q 2600/158 (2013.01); G01N 33/543 (2013.01); G01N 2800/065 (2013.01)

(58) Field of Classification Search
CPC ............ C12Q 1/2883; C12Q 2600/158; C12Q 2600/106
See application file for complete search history.

(56) References Cited

FOREIGN PATENT DOCUMENTS

WO    WO 2009/117791 A2    10/2009
WO    WO 2011/085811 A1    7/2011

OTHER PUBLICATIONS

Vivian G. Cheung, et al. "Natural variation in human gene expression assessed in lymphoblastoid cells" Nature Genetics, vol. 33, Mar. 2003, pp. 422-425 (Year: 2003).*
Tae-Hwan Kim, et al. "Gene expression profile predicting the response to anti-TNF treatment in patients with rheumatoid arthritis; analysis of GEO datasets" Joint Bone Spine vol. 81, Issue 4, Jul. 2014, pp. 325-330 (Year: 2014).*
Valérie Badot, et al. "Gene expression profiling in the synovium identifies a predictive signature of absence of response to adalimumab therapy in rheumatoid arthritis" Arthritis Research & Therapy 2009, 11:R57 (Year: 2009).*
T. Wampler Muskardin et al. "ID: 133: Single Cell Gene Expression in Classical Monocytes Correlates With Treatment Response to TNF-Alpha Inhibition in Rheumatoid Arthritis" Journal of Investigative Medicine, Mar. 22, 2016;64:976. (Year: 2016).*
Mathias Krull et al., "Transpath® : an integrated database on signal transduction and a tool for array analysis", Nucleic Acids Research, vol. 31, Issue 1, Jan. 1, 2003, pp. 97-100 (Year: 2003).*
Abraham, C. & Cho, J. H. Inflammatory Bowel Disease. *New England Journal of Medicine* 361, 2066-2078 (2009).
Adams, D. H. & Eksteen, B. Aberrant homing of mucosal T cells and extra-intestinal manifestations of inflammatory bowel disease. *Nat. Rev. Immunol.* 6, 244-251 (2006).
Agace, W. W. Tissue-tropic effector T cells: generation and targeting opportunities. *Nat. Rev. Immunol.* 6, 682-692 (2006).

(Continued)

Primary Examiner — Stephen T Kapushoc
(74) Attorney, Agent, or Firm — Cozen O'Connor

(57) ABSTRACT

The invention relates to the identification of biomarkers of the response status of a patient for a treatment with anti-TN-Falpha agents, for treatment with anti-α4β7 agents or with both anti-TNFalpha agent and anti-α4β7 agents and to their use in assessing such status, in particular for assessing nonresponsive status for a treatment with anti-TNFalpha agents or respectively with anti-α4β7 agent in human patients suffering from inflammatory condition or disease, in particular Inflammatory Bowel Disease (IBD), in particular Ulcerative Colitis or Crohn's disease. The invention describes a method of in vitro assessing whether a treatment with anti-TNFalpha agent or with anti-α4β7 agent may be useful in a human patient suffering from inflammatory condition or disease, in particular when said condition or disease is a chronic and/or relapsing one, particularly a gastrointestinal, more particularly intestinal, inflammatory condition or disease which is eligible for treatment with anti-TNFalpha agent or respectively with anti-α4β7 agent. In a specific embodiment the method is suitable to assess whether such patient would be non-responsive to treatment with such anti-TNFalpha agent or respectively with anti-α4β7 agent and comprising determining a molecular signature in a biological sample previously obtained from said human patient.

9 Claims, 7 Drawing Sheets

(56) References Cited

OTHER PUBLICATIONS

Figure 1:
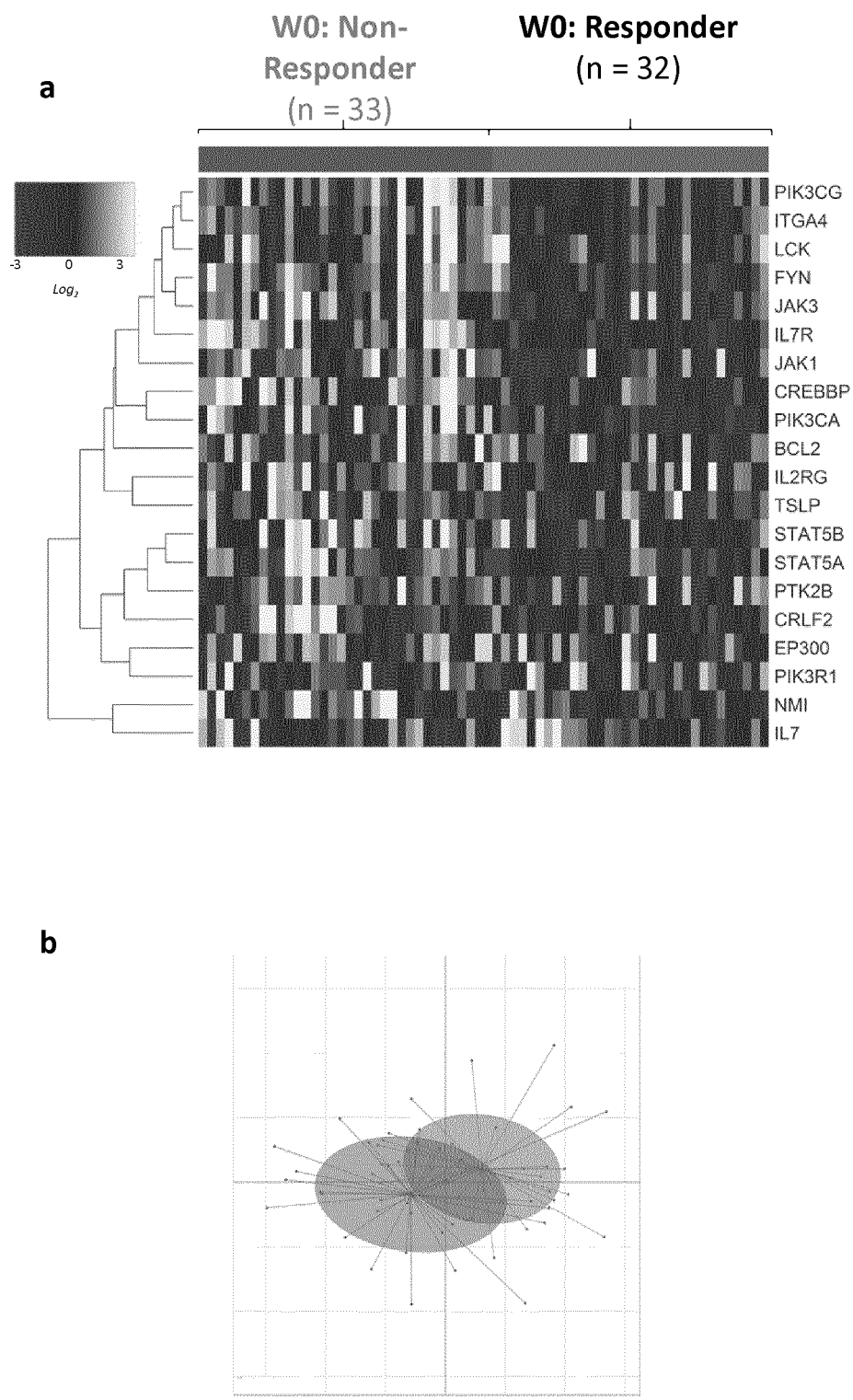
Figure 1:
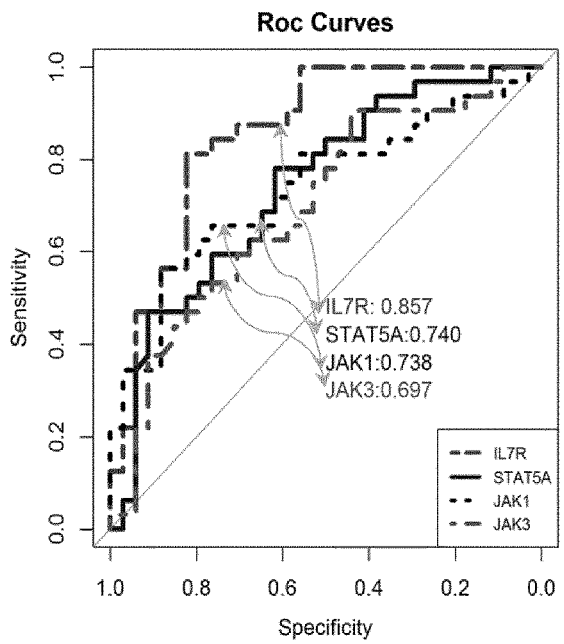
Figure 1:
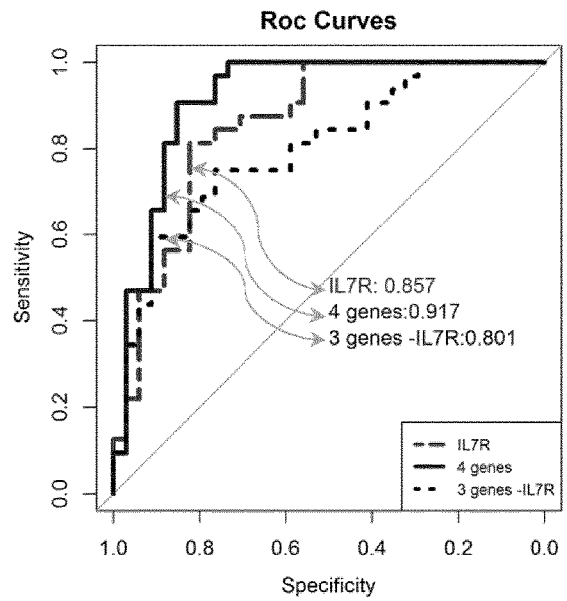
Figure 1:
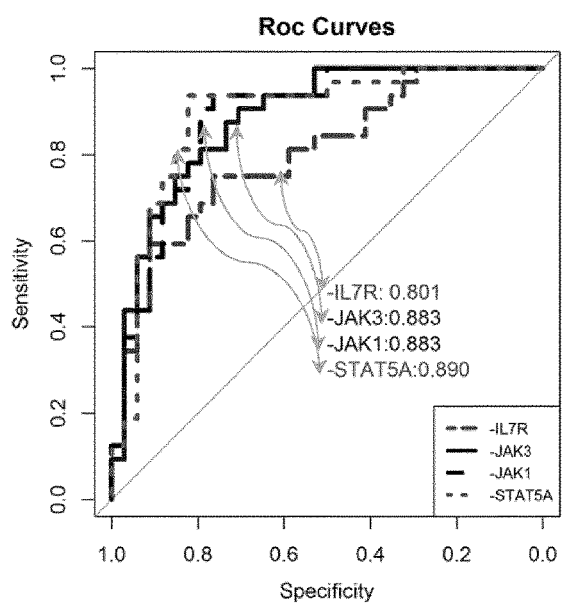
Figure 1:
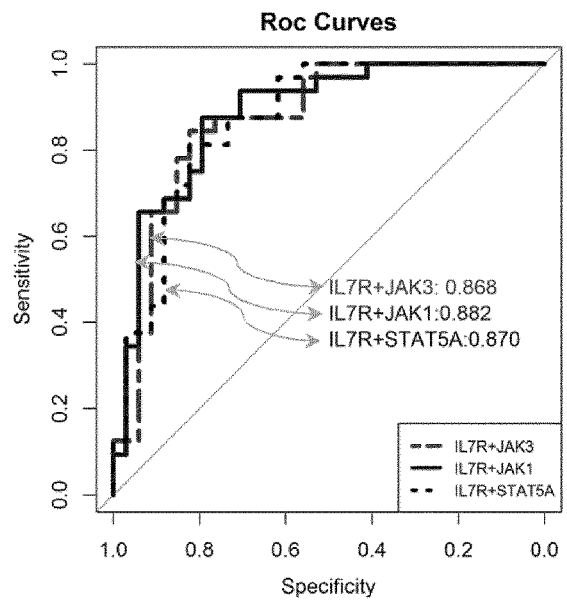

Allez, M. et al. Report of the ECCO pathogenesis workshop on anti-TNF therapy failures in inflammatory bowel diseases: definitions, frequency and pharmacological aspects. *J Crohns Colitis* 4, 355-366 (2010).

Anderson, C. A. et al. Meta-analysis identifies 29 additional ulcerative colitis risk loci, increasing the number of confirmed associations to 47. *Nat. Genet.* 43, 246-252 (2011).

Arijs, I. et al. Mucosal gene expression of antimicrobial peptides in inflammatory bowel disease before and after first infliximab treatment. *PLoS One* 4, e7984 (2009).

Arijs, I. et al. Mucosal gene signatures to predict response to infliximab in patients with ulcerative colitis. *Gut* 58, 1612-1619 (2009).

Baumgart, D. C. & Sandborn, W. J. Crohn's disease. *Lancet* 380, 1590-1605 (2012).

Bernink, J. H. et al. Human type 1 innate lymphoid cells accumulate in inflamed mucosal tissues. *Nat Immunol* 14, 221-229 (2013).

Buonocore, S. et al. Innate lymphoid cells drive interleukin-23-dependent innate intestinal pathology. *Nature* 464, 1371-1375 (2010).

Carrette, F. & Surh, C. D. IL-7 signaling and CD127 receptor regulation in the control of T cell homeostasis. *Semin. Immunol.* 24, 209-217 (2012).

Danese, S. & Fiocchi, C. Ulcerative colitis. *N. Engl. J. Med.* 365, 1713-1725 (2011).

De Souza, H. S. P. & Fiocchi, C. Immunopathogenesis of IBD: current state of the art. *Nat Rev Gastroenterol Hepatol* 13, 13-27 (2016).

Dooms, H. Interleukin-7: Fuel for the autoimmune attack. *J. Autoimmun.* 45, 40-48 (2013).

Feagan, B. G. et al. Vedolizumab as Induction and Maintenance Therapy for Ulcerative Colitis. *New England Journal of Medicine* 369, 699-710 (2013).

Goldberg, R., Prescott, N., Lord, G. M., MacDonald, T. T. & Powell, N. The unusual suspects—innate lymphoid cells as novel therapeutic targets in IBD. *Nat Rev Gastroenterol Hepatol* 12, 271-283 (2015).

Haberman, Y. et al. Pediatric Crohn disease patients exhibit specific ileal transcriptome and microbiome signature. *J. Clin. Invest.* 124, 3617-3633 (2014).

Johnson WE, Li C, Rabinovic A. Adjusting batch effects in microarray expression data using empirical Bayes methods. *Biostatistics* 2007;8(1):118-127.

Khor, B., Gardet, A. & Xavier, R. J. Genetics and pathogenesis of inflammatory bowel disease. *Nature* 474, 307-317 (2011).

Lee, J. C. et al. Gene expression profiling of CD8+ T cells predicts prognosis in patients with Crohn disease and ulcerative colitis. *J. Clin. Invest.* 121, 4170-4179 (2011).

Liu, W. et al. CD127 expression inversely correlates with FoxP3 and suppressive function of human CD4+ T reg cells. *J. Exp. Med* 203, 1701-1711 (2006).

MacDonald, T. T., Biancheri, P., Sarra, M. & Monteleone, G. What's the next best cytokine target in IBD? *Inflamm Bowel Dis* 18, 2180-2189 (2012).

Mackall, C. L., Fry, T. J. & Gress, R. E. Harnessing the biology of IL-7 for therapeutic application. *Nat. Rev. Immunol.* 11, 330-342 (2011).

Mai, H.-L. et al. IL-7 receptor blockade following T cell depletion promotes long-term allograft survival. *J. Clin. Invest.* 124, 1723-1733 (2014).

Mazzucchelli, R. & Durum, S. K. Interleukin-7 receptor expression: intelligent design. *Nat. Rev. Immunol.* 7, 144-154 (2007).

Michel, L. et al. Patients with relapsing-remitting multiple sclerosis have normal Treg function when cells expressing IL-7 receptor alpha-chain are excluded from the analysis. *J. Clin. Invest.* 118, 3411-3419 (2008).

Neurath, M. F. Cytokines in inflammatory bowel disease. *Nat Rev Immunol* 14, 329-342 (2014).

Newman AM et al. Robust enumeration of cell subsets from tissue expression profiles. *Nat. Methods* 2015;12(5):453-457.

Okada, E. et al. IL-7 exacerbates chronic colitis with expansion of memory IL-7Rhigh CD4+ mucosal T cells in mice. *Am. J. Physiol. Gastrointest. Liver Physiol.* 288, G745-754 (2005).

Planell, N. et al. Transcriptional analysis of the intestinal mucosa of patients with ulcerative colitis in remission reveals lasting epithelial cell alterations. *Gut* 62, 967-976 (2013).

Powell, N. et al. The transcription factor T-bet regulates intestinal inflammation mediated by interleukin-7 receptor+ innate lymphoid cells. *Immunity* 37, 674-684 (2012).

Robin, X. et al. pROC: an open-source package for R and S+ to analyze and compare ROC curves. *BMC Bioinformatics* 12, 77 (2011).

Rochman, Y., Spolski, R. & Leonard, W. J. New insights into the regulation of T cells by gamma(c) family cytokines. *Nat. Rev. Immunol.* 9, 480-490 (2009).

Sandborn, W. J. et al. Vedolizumab as Induction and Maintenance Therapy for Crohn's Disease. *New England Journal of Medicine* 369, 711-721 (2013).

Seddiki, N. et al. Expression of interleukin (IL)-2 and IL-7 receptors discriminates between human regulatory and activated T cells. *J. Exp. Med.* 203, 1693-1700 (2006).

Shalapour, S. et al. Commensal microflora and interferon-gamma promote steady-state interleukin-7 production in vivo. *Eur. J. Immunol.* 40, 2391-2400 (2010).

Shalapour, S. et al. Interleukin-7 links T lymphocyte and intestinal epithelial cell homeostasis. *PLoS One* 7, e31939 (2012).

Shinohara, T. et al. Upregulated IL-7 receptor α expression on colitogenic memory CD4+ T cells may participate in the development and persistence of chronic colitis. *J. Immunol.* 186, 2623-2632 (2011).

Smyth, G. K. Linear models and empirical bayes methods for assessing differential expression in microarray experiments. *Stat Appl Genet Mol Biol* 3, Article3 (2004).

The ade4 Package: Implementing the Duality Diagram for Ecologists | Dray | Journal of Statistical Software [Internet] doi:10.18637/jss.v022.i04.

Toedter, G. et al. Gene expression profiling and response signatures associated with differential responses to infliximab treatment in ulcerative colitis. *Am. J. Gastroenterol.* 106, 1272-1280 (2011).

Torres, J., Mehandru, S., Colombel, J.-F. & Peyrin-Biroulet, L. Crohn's disease. *Lancet* 389, 1741-1755 (2017).

Totsuka, T. et al. IL-7 Is essential for the development and the persistence of chronic colitis. *J. Immunol.* 178, 4737-4748 (2007).

Ungaro, R., Mehandru, S., Allen, P. B., Peyrin-Biroulet, L. & Colombel, J.-F. Ulcerative colitis. *Lancet* 389, 1756-1770 (2017).

Vanhove, W. et al. Strong Upregulation of AIM2 and IFI16 Inflammasomes in the Mucosa of Patients with Active Inflammatory Bowel Disease. *Inflamm. Bowel Dis.* 21, 2673-2682 (2015).

Watanabe, M. et al. Interleukin 7 is produced by human intestinal epithelial cells and regulates the proliferation of intestinal mucosal lymphocytes. *J. Clin. Invest.* 95, 2945-2953 (1995).

Watanabe, M. et al. Interleukin 7 transgenic mice develop chronic colitis with decreased interleukin 7 protein accumulation in the colonic mucosa. *J. Exp. Med.* 187, 389-402 (1998).

Willis, C. R. et al. Interleukin-7 receptor blockade suppresses adaptive and innate inflammatory responses in experimental colitis. *J Inflamm (Lond)* 9, 39 (2012).

Yamazaki, M. et al. Mucosal T cells expressing high levels of IL-7 receptor are potential targets for treatment of chronic colitis. *J. Immunol.* 171, 1556-1563 (2003).

International Patent Application No. PCT/EP2018/071206, International Search Report and Written Opinion dated Sep. 21, 2018, 17 pgs.

Arijs et al. (2009), "Mucosal gene signatures to predict response to infliximab in patients with ulcerative colitis", Gut, British Medical Association, London, UK, vol. 58, No. 12, Dec. 1, 2009 (Dec. 1, 2009), pp. 1612-1619.

Wang Yue et al. (2015), "Gene expression profile predicting the response to anti-TNF antibodies therapy in patients with inflam-

(56) References Cited

OTHER PUBLICATIONS matory bowel disease: analyses of GEO datasets" International Journal of Clinical and Experimental Medicine 2015, E-Century Publishing Corporation, US.

Hummert C et al. (2011), "Creation and Comparison of Different Chip Definition Files for Affymetrix Microarrays", 2011 International Conference on Bioinformatics & Computational Biology Biocomp 2011, Jul. 18-21, 2011, Las Vegas NV, vol. 1, Jan. 1, 2011 (Jan. 1, 2011), pp. 16-22.

Belarif L et al. (2018), "Interleukin-7 receptor pathway controls human T cell homing to the gut and predicts response to anti-TNF[alpha] therapy in IBD", Journal of Immunology May 1, 2018 American Association of Immunologists NLD, vol. 200, No. 1, Supplement 1, May 1, 2018 (May 1, 2018); ISSN: 1550-6606.

C. Hummert et al. (Jul. 2011), "Creation and Comparison of Different Chip Definition Files for Affymetrix Microoarrays", Int'l Cont. Bioinformatics and Computational Biology | BIOCOMP'11, pp. 16-22.

* cited by examiner c

| Univariate analysis | | | | | | Multivariate analysis | |
|---|---|---|---|---|---|---|---|
| ID | logFC | AveExpr | adj.P.Val | AUC | AUC with IL7R | p-value | |
| IL7R | 1,59 | 0,856 | 0,0000001 | 0,8566176 | / | 0,00035 | *** |
| STAT5A | 0,93 | 0,366 | 0,0040 | 0,7403 | 0,863 | 0,0258 | * |
| CREBBP | 1,07 | 0,607 | 0,0040 | 0,7233 | 0,833 | ns | |
| FYN | 0,90 | 0,427 | 0,0069 | 0,7688 | 0,834 | ns | |
| JAK1 | 0,81 | 0,105 | 0,010 | 0,738 | 0,870 | 0,0127 | * |
| STAT5B | 0,93 | 0,645 | 0,013 | 0,706 | 0,819 | ns | |
| JAK3 | 0,70 | 0,170 | 0,016 | 0,697 | 0,812 | 0,0119 | * |
| PIK3CG | 0,68 | 0,277 | 0,018 | 0,721 | 0,824 | ns | |
| PIK3CA | 0,83 | 0,380 | 0,018 | 0,670 | 0,791 | ns | |
| NMI | 0,82 | 0,186 | 0,034 | 0,629 | 0,830 | ns | |
| CRLF2 | 0,84 | 0,423 | 0,034 | 0,572 | 0,796 | ns | |
| ITGA4 | 0,56 | 0,073 | 0,035 | 0,689 | 0,824 | ns | |
| IL7 | -0,56 | 0,037 | 0,13 | 0,66 | 0,63 | ns | |
| PIK3R1 | -0,46 | -0,045 | 0,17 | 0,59 | 0,67 | ns | |
| IL2RG | 0,35 | 0,207 | 0,24 | 0,64 | 0,83 | ns | |
| EP300 | 0,36 | 0,291 | 0,27 | 0,59 | 0,83 | ns | |
| TSLP | 0,29 | -0,155 | 0,30 | 0,62 | 0,83 | ns | |
| LCK | 0,27 | 0,316 | 0,35 | 0,59 | 0,77 | ns | |
| PTK2B | 0,13 | -0,075 | 0,63 | 0,59 | 0,81 | ns | |
| BCL2 | -0,12 | 0,040 | 0,68 | 0,54 | 0,68 | ns | |

Figure 1 d e f g

BIOMARKERS FOR ASSESSING THE RESPONSE STATUS FOR TREATMENT OF INFLAMMATORY CONDITION OR DISEASE AFFECTING THE DIGESTIVE TRACT SUCH AS INFLAMMATORY BOWEL DISEASE IN HUMAN PATIENTS

CROSS-REFERENCE TO RELATED APPLICATIONS

This application is a 35 U.S.C. § 371 filing of International Application No. PCT/EP2018/071206 filed Aug. 3, 2018, which claims the benefit of priority to European Patent Application No. 17306039.3 filed Aug. 3, 2017, each of which is incorporated herein by reference in its entirety.

The invention relates to the identification of biomarkers of the response status of a patient in need of treatment of an inflammatory condition or disease affecting the digestive tract such as Inflammatory bowel disease (IBD) such as ulcerative colitis (UC) and Crohn's disease (CD), which are chronic (especially relapsing) gastrointestinal disorders characterized by chronic intestinal inflammation.

The invention also relates to the identification of biomarkers of the response status of a patient for a treatment with anti-TNFalpha agents for treatment with anti-α4β7 agents or with both anti-TNFalpha agent and anti-α4β7 agent and to their use in assessing such status, in particular for assessing nonresponsive status for a treatment with anti-TNFalpha agents in human patients suffering from inflammatory condition or disease.

The invention accordingly describes a method of in vitro assessing whether a human patient suffering from inflammatory condition or disease, in particular when said condition or disease is a chronic and/or relapsing one, and when said condition or disease is eligible for treatment with anti-TNFalpha agent, or is eligible for treatment with anti-α4β7 agent or with both anti-TNFalpha agent and anti-α4β7 agent, may usefully be treated with such anti-TNFalpha agent or is eligible for treatment with anti-α4β7 or with both anti-TNFalpha agent and anti-α4β7. In a particular aspect of the invention, the method is a method of assessing whether such human patient would be non-responsive to treatment by an anti-TNFalpha agent or is eligible for treatment with anti-α4β7 or with both anti-TNFalpha agent and anti-α4β7. In a first aspect of the invention, the method comprises determining in a biological sample previously obtained from said human patient, the expression profile, in particular determining the transcripts profile, for at least one gene selected from the group of IL7R, FYN, STAT5A, JAK1, CREBBP, PIK3CG, STAT5B, JAK3, ITGA4, PIK3CA, NMI and CRLF2 genes or at least two genes in said group wherein one gene is IL7R and one further gene in said group is preferably JAK1. The targeted condition or disease is one which is eligible for treatment with anti-TNFalpha agents or is eligible for treatment with anti-α4β7 or with both anti-TNFalpha agent and anti-α4β7; in particular it is a chronic (particularly relapsing) inflammatory condition or disease, especially one affecting the digestive tract and more particularly a condition or disease affecting the gastrointestinal, especially intestinal system.

In a further aspect of the invention, the method comprises determining in a biological sample previously obtained from said human patient, the expression profile, in particular determining the transcripts profile, for at least two genes wherein one gene is IL7R and at least one gene is selected in the group of selected from the group of JAK1, IL2RG, PIK3CA, NMI, CRLF2, LCK, BCL2, EP300 and TSLP genes, in particular wherein the at least one further gene comprises JAK1 gene from said group.

The invention also relates to the use of the biomarkers disclosed herein in a method for assessing the responsiveness status of a patient suffering from a condition or a disease which is an Inflammatory bowel disease (IBD) such as ulcerative colitis (UC) and Crohn's disease (CD).

The invention also relates to means suitable for carrying out the method and in particular to probes that specifically hybridize to the transcript of each gene or to nucleic acids derived therefrom. It also relates to antibodies, fragments thereof and derivatives that may contain them suitable for the detection of proteins expressed by the target gene(s).

Treatment options associated with the different conditions and diseases targeted in accordance with the invention may in particular take into account the fact that such diseases or condition are characterized as being eligible to treatment by anti-TNFalpha agents or is eligible for treatment with anti-α4β7 agent or with both anti-TNFalpha agent and anti-α4β7 agent, especially inflammatory condition or disease (which may be chronic) primarily aim at decreasing the symptoms and especially the inflammation process. In a particular embodiment, these treatments involve multiple classes of agents that may precede the use of anti-TNFalphe agents or anti-α4β7 agent, especially anti-inflammatory agents including as a primary option current conventional treatment aiming at dampening inflammation through the use of anti-inflammatory agents, steroids, immunosuppressive drugs, and as a further option when the disease remains active or is resistant to such drugs biological agents targeting inflammatory cytokines and accordingly mainly anti-tumor necrosis factor alpha (TNFα) (anti-TNFalpha agents also designated TNFalpha inhibitors) or α4β7 integrin.

TNFα (Tissue Necrosis Factor alpha) causes pro-inflammatory actions that may evolve toward many types of diseases or conditions in human and in particular toward inflammatory diseases, especially chronic inflammatory diseases. TNFalpha has thus become a therapeutic target to treat such diseases and agents that block or inhibit TNFalpha activity in vivo have proved successful at least in part.

It has been observed however that patients do not always show clinical benefits from a treatment with anti-TNFalpha agents or do not benefit from such treatment on long-term, especially suffer from relapse of their disease or condition after a few weeks of treatment and despite an initial adequate response.

Similarly, it has been observed that patients affected with these diseases or conditions may show benefit from a treatment with anti-α4β7 therapy unless they show resistance to such therapy.

It has in particular been observed in the case of severe forms or refractory forms of chronic gastrointestinal inflammatory diseases such as Inflammatory bowel disease (IBD) (that consists of two major forms i.e., ulcerative colitis (UC) and Crohn's disease (CD), which are chronic (especially relapsing) gastrointestinal disorders characterized by chronic intestinal inflammation) approximately one-third of patients receiving anti-TNFα agents do not respond to treatment (primary failure), and a significant proportion (up to 50%) become refractory over time (secondary failure)[7].

In view of the uncertainty on the positive outcome of the treatment with anti-TNFalpha agents, there is a need to improve prescription of such treatment by selecting the patients likely to respond, also to avoid administering to a patient a treatment that may raise side effects without the expected clinical benefits. Besides due to the expensive cost of treatments with anti-TNFalpha agents there is a collective interest to select patients for treatment who may effectively clinically benefit from its administration.

Accordingly there is a need in the art for methods suitable for assessing whether an adequate response to a treatment with anti-TNFalpha agents or treatment with anti-α4β7 agents is likely to be expected in a patient, prior to give this treatment.

The inventors have studied the signaling networks perpetuating chronic gastrointestinal inflammation in Crohn's disease (CD) and ulcerative colitis (UC), the two main forms of inflammatory bowel diseases (IBD), that remain unclear in man. According to an analysis of nearly 500 patients with IBD and 100 controls, they report here that key transcripts specific genes, including especially transcripts of the IL-7 receptor (IL-7R) pathway accumulate in inflamed colon tissues of severe IBD patients not responding to either immunosuppressive/corticosteroids or anti-TNFα or anti-α4β7 therapies. Hence the inventors have characterized that high expression of both IL-7R and IL-7R signaling signature transcripts in the colon before treatment are strongly associated with non-responsiveness to anti-TNFα or to anti-α4β7 therapy.

The invention accordingly relates to a method of in vitro assessing the response status of a human patient for a treatment with anti-TNFalpha agent and/or to anti-α4β7 agent, wherein said patient is suffering from a condition or disease which is eligible for treatment with anti-TNFalpha agent, or is eligible for treatment with anti-α4β7 or with both anti-TNFalpha agent and anti-α4β7, in particular is suffering from inflammatory condition or disease which is Inflammatory Bowel Disease (IBD), in particular Ulcerative Colitis or Crohn's disease, wherein the method comprises:
  a/ in a biological sample previously obtained from said human patient, determining the expression profile, in particular determining the transcripts profile, of a set of genes comprising at least two genes wherein one gene is IL7R and at least one gene is selected in the group of FYN, STAT5A, JAK1, CREBBP, PIK3CG, STAT5B, JAK3, ITGA4, PIK3CA, NMI and CRLF2 genes, in particular wherein at least one gene in said group is JAK1,
  b/ comparing said expression profile of step (a), in particular said transcripts profile, to a reference and determining the difference or the similarity in expression profile with respect to such reference and deriving the response status of the patient from said difference or similarity,
whereby optionally when said at least two genes, are overexpressed with respect to said reference or by contrast are not overexpressed with respect to said reference, a statement is derived on the response status of the patient to a treatment with anti-TNFalpha agent or respectively to anti-α4β7 agent.

within the present invention, the targeted disease or condition is in particular Inflammatory Bowel Disease (IBD), in particular Ulcerative Colitis or Crohn's disease. In order to carry out the methods of the invention, it may be appropriate or sufficient that the condition or the disease suspected, detected or diagnosed in the patient is one which is known as a condition or a disease eligible for treatment with anti-TNFα agent or with anti-α4β7 agent according to clinical practice. Otherwise stated the patient needs not necessary to undergo specific assessment of the category of the disease or condition that has been suspected, detected or diagnosed to issue a conclusion on eligibility. In particular when the condition or disease is suspected, detected or diagnosed as being one among those especially specified herein (such as IBD), the methods of the invention may be carried out without a need for a biological or clinical step of determination of eligibility that is hence considered implicit.

Determining the "response status" of a patient should be understood as the possibility, based on the herein disclosed assessment or on this assessment in combination with additional tests, or in combination with observation of the severity of clinical symptoms in the patient or in combination with risk factors, to provide an indication or a conclusion that the patient is likely or not likely to derive benefits from a treatment with anti-TNFalpha agent or with anti-α4β7 agent. It may also encompass the use of the method herein disclosed to enable the decision to prescribe further tests of distinct biological or clinical parameters that may confirm or supplement the indication provided by the method of the invention. The response status of a patient intends to provide guidance on the usefulness of a treatment with anti-TNF agent in this patient or with anti-α4β7 respectively.

The targeted disease or condition to perform the methods of the invention is in particular Inflammatory Bowel Disease (IBD), in particular Ulcerative Colitis or Crohn's disease.

In a particular aspect, the invention thus relates to a method to assess or to discriminate the status of non-responsiveness of a human patient for a treatment with anti-TNFalpha agent and/or to anti-α4β7 agent, wherein the patient is suffering from a condition or disease which is eligible for treatment with anti-TNFalpha agent, or is eligible for treatment with anti-α4β7 agent or with both anti-TNFalpha agent and anti-α4β7 agent, in particular is suffering from, particularly chronic and/or relapsing, inflammatory condition or disease which is Inflammatory Bowel Disease (IBD), in particular Ulcerative Colitis or Crohn's disease, said method comprising:
  a. in a biological sample previously obtained from said human patient, determining the expression profile, in particular determining the transcripts profile, of a set of genes comprising at least two genes wherein one gene is IL7R and at least one gene is selected in the group of FYN, STAT5A, JAK1, CREBBP, PIK3CG, STAT5B, JAK3, ITGA4, PIK3CA, NMI and CRLF2 genes, in particular wherein at least one gene in said group is JAK1
  b. comparing said expression profile of step (a), in particular said transcripts profile, to a reference,
in particular whereby when said at least one gene, in particular at least two genes are overexpressed with respect to a reference featuring the expression profile of the gene(s) of a healthy standard or are expressed similarly to a reference featuring a non-responsive standard to anti-TNFalpha agent or to anti-α4β7 agent, such expression profile is discriminative for non-responsiveness to anti-TNFalpha agent or respectively to anti-α4β7 agent.

The invention also concerns a method of in vitro assessing the response status, in particular of assessing the non-responsiveness for a treatment with anti-TNFalpha agent and/or to anti-α4β7 agent of a human patient suffering from an inflammatory condition or disease which is Inflammatory Bowel Disease (IBD), in particular Ulcerative Colitis or Crohn's disease, said method comprising:
  a. in a biological sample previously obtained from said human patient, determining the expression profile, in particular determining the transcripts profile, of a set of genes comprising at least two genes wherein one gene is IL7R and at least one gene is selected in the group of JAK1, IL2RG, PIK3CA, NMI, CRLF2, LCK, BCL2, EP300 and TSLP genes, in particular wherein the at least one gene in said group comprises JAK1 b. comparing said expression profile of step (a), in particular said transcripts profile, to a reference, in particular whereby when said at least two genes are overexpressed or underexpressed with respect to a reference featuring the expression profile of the gene(s) of a healthy standard or are expressed similarly to a reference featuring a non-responsive standard to anti-TNFalpha agent or to anti-α4β7 agent, such expression profile is discriminative for non-responsiveness to anti-TNFalpha agent or respectively to anti-α4β7 agent.

The "expression profile" in accordance with the one gene or the set of genes (meaning at least two genes) encompasses or is the expression levels (either qualitative or quantitative) of the target gene(s). These expression levels can be determined by detecting the levels of the gene products, for example the transcript levels (profile) or the protein levels (profile) wherein the proteins are expressed from the tested gene(s). Accordingly the expression profile may be detected by any suitable means involving nucleic acids recognizing specifically the target gene(s), including nucleotide probes or means suitable for the detection of the proteins encoded by the target gene(s), such means encompassing antibodies (or fragments thereof) binding specifically the proteins. In the context of the present invention, a reagent (e.g., a probe, a primer or an antibody) is "specific" for its target or "binds specifically" or "hybridizes specifically" to its target if it exhibits a threshold level or capacity of binding activity, and/or it does not significantly cross-react with known related molecules. One skilled in the art can readily determine said binding capacity.

The "reference" can be the expression profile of the same gene(s) as the gene(s) assessed in the human patient, that is characteristic of a healthy status (so-called healthy standard) as far as the conditions or disease is concerned, in particular healthy with respect to an inflammatory condition or disease (particularly a chronic one), especially digestive condition of disease, especially chronic gastrointestinal, in particular intestinal, inflammatory conditions or disease such as Inflammatory Bowel Disease (IBD), in particular Ulcerative Colitis or Crohn's disease. Such reference is in particular suitable for use when it is sought whether the expression profile of the genes is typical of overexpression or rather is typical of no-overexpression (e.g. similarity of expression) or is typical of under-expression for the genes which have been detected as being expressed at a lower level (under-expressed), such as TSLP, IL2RG, LCK, BCL2 and EP300. Alternatively, the reference may be the expression profile of the same gene(s) as the gene(s) retrieved from a sample such as from a biopsie, a biological fluid or cells (including blood cells), or from data gathered from samples of patient(s) suffering from a condition or disease identical or of a similar type to the one assessed in the tested patient. In a particular embodiment the expression profile is representative of a non-responsive status (so called non-responsive standard). Expression profiles as defined herein may especially be of interest when it is sought whether overexpression characteristic of a non-responsive status is found in the expression profile of the patient. Alternatively for other genes of the selection such as TSLP, IL2RG, LCK, BCL2 and EP300, expression profile as defined herewith may especially be of interest when it is sought whether under-expression of the gene(s) is characteristic of a non-responsive status. The expression profile of the gene(s) of interest in accordance with the invention in the reference may be determined on a single biological sample or on a pool of biological samples, such samples being for example blood cells or tissue sample such as tissue sample obtained from biopsies. Alternatively the expression profile may be retrieved from a pre-established reference cohort. In an embodiment, the reference enables the quantification of the expression of the target genes assessed in the expression profile of the patient. The quantification may be relative with respect to the expression profile of the reference or may be absolute. In a particular embodiment the reference may be provided as a collection of plasmids wherein each plasmid is recombined with the sequence of one target gene wherein such collection enables absolute quantification of the patient's expression profile. Alternatively the standard may be a collection of proteins expressed by the target genes and quantitated by any known method such as ELISA. When it is indicated that the expression is "similar" to the expression in a reference it means that the level of expression is identical or is in the same order of magnitude, i.e., is not significantly different and as a consequence may be regarded as illustrative of the same category of responsive status for the patient as the reference.

In a particular embodiment, the expression profile of genes and the reference for such expression profile especially targets the assessment of the status of the patient for anti-TNF therapy.

In a particular embodiment, the assessment of the status of non-responsiveness of a patient enables also a conclusion regarding the fact that the patient will be responsive to the proposed or targeted treatment when the said assessment of non-responsiveness has allowed to conclude that the patient would not be non-responsive. In this regard, the invention also provides a method of determining whether a patient would be responsive to anti-TNF therapy or to anti-α4β7 therapy.

According to this method the expression profile of at least two genes, in particular of a set of at least two and preferably more than two genes (that comprises at least two genes including IL7R gene and optionally also JAK1) is determined. Accordingly the expression of the gene(s) is quantitated, in particular by quantitation of the gene(s) transcript or expressed protein. The method then encompasses comparison of the expression profile of each assessed gene with a reference and determination of the response status. In a particular embodiment it is determined whether overexpression of said gene is detected with respect to said reference when this reference is a healthy standard. Overexpression means that the expression level of said gene is higher than the expression level of the same gene in the reference if the reference provides expression profile of a healthy subject. Overexpression may encompass an expression level above 50% or more than 50% with respect to the expression level in a reference when the reference provides expression profile of a healthy subject. In another particular embodiment it is determined whether underexpression of a gene in particular from the group of TSLP, IL2RG, LCK, BCL2 and EP300 genes is detected with respect to a reference when this reference is a healthy standard. Underexpression means that the expression level of said gene is lower than the expression level of the same gene in the reference if the reference provides expression profile of a healthy subject.

The method defined herein assesses the response status of a patient in the above described medical context. The patient is a human patient and is either an adult or a pediatric patient (i.e. a patient under the age of 18).

The method of the invention is performed in vitro and is intended for assessing the usefulness of a treatment with anti-TNFalpha agent or with anti-α4β7 agent in patients suffering, especially suspected, detected or diagnosed, for a condition or disease which is one specified in the present disclosure such as IBD and in particular UC or CD or more generally is one eligible for treatment by anti-TNFα agent or with anti-α4β7 agent and in particular is an inflammatory TNFα-mediated pathology or an inflammatory α4β7-mediated pathology. In particular the method of the invention is used for discrimination of non-responsive patients who have been suspected, detected or diagnosed as suffering from an inflammatory pathology, in particular a chronic and/or relapsing one in particular one of the pathologies disclosed herein such as especially Inflammatory Bowel Disease (IBD), in particular Ulcerative Colitis or Crohn's disease.

In particular the methods of the invention are carried out to determine the response status of a patient suffering from a disease or condition affecting the digestive tract, especially is a gastrointestinal pathology, in particular a chronic inflammatory gastrointestinal or intestinal pathology, and more particularly a pathology wherein the patient suffers from relapse, i.e., reappearance of symptoms of the pathological state despite therapeutic or prophylactic treatment, such as observed in some patients suffering from IBD and in particular UC or CD. In a particular embodiment, the methods of the invention are carried out to determine the response status of a patient who suffers from a condition or disease eligible for treatment with anti-TNF agent, or with anti-α4β7 agent and which is an inflammatory condition or disease of the digestive tract, in particular a gastrointestinal inflammatory disease or condition, particularly is a disease or condition selected from Inflammatory Bowel Disease (IBD) such as Ulcerative Colitis, Crohn's disease, pediatric Crohn disease, pediatric Ulcerative Colitis or, eosinophilic esophagitis, celiac disease. In another embodiment the patient is suffering from an inflammatory, in particular a chronic, a condition or disease among rheumatoid polyarthritis, juvenile idiopathic arthritis, psoriatic arthritis, ankylosing spondylitis, plaque psoriasis, pediatric plaque psoriasis, polyarticular juvenile idiopathic arthritis, axial spondyloarthritis ankylosing spondylitis, psoriasis, hydradenitis suppurativa. This condition or disease may be a relapsing one, in particular when it is Inflammatory Bowel Disease (IBD), in particular Ulcerative Colitis or Crohn's disease.

In a more particular embodiment, the patient suffers from a condition or disease eligible for treatment with anti-TNF agent or with anti-α4β7 agent, which is a chronic inflammatory condition or disease of the digestive tract, in particular a chronic gastrointestinal inflammatory disease, more particularly a chronic intestinal inflammatory disease, preferably is Inflammatory Bowel Disease (IBD) in particular Ulcerative Colitis or Crohn's disease or eosinophilic esophagitis or celiac disease.

In a more particular embodiment, the patient suffers from a condition or disease eligible for treatment with anti-TNF agent, which is Inflammatory Bowel Disease (IBD), in particular Ulcerative Colitis or Crohn's disease.

According to a particular embodiment of the invention, determining that a patient would be non-responsive according to the method of the invention enables to conclude that the likelihood of positive outcome is significantly less than the likelihood of failure of an anti-TNF treatment or anti-α4β7 treatment in accordance with the criteria known in the field for the considered disease or condition in such particular patient.

The expressions "anti-TNFalpha agent" or "anti-TNFalpha treatment" may be used interchangeably in the present disclosure to designate compounds, i.e. biological or chemical compounds or mixtures of such compounds, whether authorized as drug or formulated as pharmaceutical agent for administration to a patient that are known, medically recognized or tested to block or inhibit TNFalpha activity in vivo. "Anti-TNFalpha agents" are of multiple types and known in the art, especially as approved drugs. They include chemical or biological molecules, in particular anti-TNFalpha antibodies that specifically bind to TNFalpha and inhibit its activity in vivo. They include also soluble TNFalpha receptor or antibodies binding to TNFalpha receptor. Examples of anti-TNFalpha agents include but are not limited to inhibitors of TNFalpha synthesis, inhibitors of TNFalpha release, inhibitors of TNFalpha activity, inhibitors of TNFalpha signaling and, to illustrate, include thalidomide, tenidap, phosphodiesterase inhibitors, antibodies or recombinant proteins specifically binding to TNFalpha such as infliximab, golimumab, adalimumab, certolizumab-pegol or etanercept.

The expressions "anti-α4β7 agent" or "anti-α4β7 treatment" may be used interchangeably in the present disclosure to designate compounds, i.e. biological or chemical compounds or mixtures of such compounds, whether authorized as drug or formulated as pharmaceutical agent for administration to a patient that are known, medically recognized or tested to block or inhibit α4β7 integrin activity in vivo. vedolizumab is one of the known anti-α4β7 agents used in the concerned diseases or conditions of the invention.

The expressions «non-responsive», «non-responsiveness» according to the invention encompass the status of a human patient who experiences failure (or would experience failure if treated) to raise a beneficial clinical response to a treatment by an anti-TNFalpha agent or by an anti-α4β7 agent also otherwise stated as failure to respond to anti-TNFalpha or respectively to anti-α4β7 treatment. Accordingly stable disease or progressive disease after treatment would be considered non-responsive to treatment. The non-responsiveness may be observed in a patient who does not respond to the treatment when it is first performed (primary failure). A non-responsive patient may alternatively be a patient who does not respond to the treatment over time (in particular after a few weeks of treatment) and accordingly a patient who relapses (secondary failure). Failure to respond to the treatment may thus be detected early in the course of the treatment and accordingly may be seen as clinically active or stable disease after less than 10 weeks of treatment, for example 8 weeks of treatment. Failure to respond to the treatment may be detected late in the course of the treatment and accordingly may be determined as clinically active or stable disease after more than 10 weeks, especially more than 20 or more than 30 weeks of treatment. Active disease is characterized in accordance with the criteria known in the art for the concerned disease and in particular is determined on the basis of clinical and optionally where appropriate endoscopic or histological findings (such as performed in patients with IBD). A non-responsive patient is more generally seen as a patient who suffers from a disease or condition as disclosed herein with relapse or clinical signs of a refractory disease. As a consequence a patient is non responsive in accordance with the method of the invention when he/she is at risk of facing a situation as described above in case an anti-TNFalpha treatment or in case an anti-α4β7 treatment respectively is or would be administered to him/her.

The term "treatment" according to the invention applies to the administration of anti-TNFalpha agent(s) to a human patient for the purpose of improving the clinical signs and symptoms related to, in particular caused by the condition or disease or to lessen or stabilize or cure of the condition or disease or enable remission of the patient and in any case "treatment" encompasses beneficial clinical response to the administration of the anti-TNFalpha agent of the anti-α4β7 agent for a patient in relation to the suspected, detected or diagnosed, inflammatory condition or disease, in particular chronic and/or relapsing condition or disease, including especially condition or disease affecting the digestive tract such as gastrointestinal, in particular intestinal, inflammatory condition or disease. The term "treatment" also applies to the beneficial results expected from the administration of anti-TNFalpha agent(s) or of anti-α4β7 agent(s), i.e., the improvement of the symptoms related to the condition or disease or the decrease or stabilization or healing of the condition or disease or the remission status of the patient and in any case the clinical benefit for the patient in relation to the diagnosed inflammatory condition or disease, in particular chronic and/or relapsing condition or disease, including especially condition or disease affecting the digestive tract such as, gastrointestinal, in particular intestinal, inflammatory condition or disease. Additionally the term "treatment" also applies to the administered agent when used in the expression anti-TNFalpha treatment or anti-α4β7 treatment respectively.

According to an embodiment of the method of the invention, the expression profile of a gene or a set of genes is said to be "discriminative for non-responsiveness to anti-TNFalpha agent" or "discriminative for non-responsiveness to anti-α4β7 agent" when in particular this profile departs, especially quantitatively departs, from the expression profile of a reference gene or set of genes comprising the same genes as the assayed gene(s) and accordingly shows overexpression of said gene or genes or in case of genes from the group of TSLP, IL2RG, LCK, BCL2 and EP300, underexpression of said gene(s) of said set with respect to the reference which is illustrative of a healthy standard, in particular showing accumulation of mRNA transcripts of said gene(s). In another embodiment, when the reference is illustrative of the expression profile of a non-responsive patient, the tested expression profile is discriminative for non-responsiveness when it is similar to the reference. Accordingly the expression profile enables classification of the patient as likely not to benefit clinically from a treatment with anti-TNFalpha agent or with anti-α4β7 agent, i.e. if treated the patient would not have a positive global physician's assessment of disease activity or would show persistent signs and symptoms of the disease state. Accordingly the non-responsive status of the human patient may be acknowledged on the basis of the sole result relating to the expression profile of the considered genes disclosed herein. Alternatively the non-responsive status may be acknowledged when the result obtained from performing the method of the invention in respect of said gene(s) is associated with the measurement or assessment of additional clinical or physiological parameters and this association is predictive of a failure to respond to an anti-TNFalpha treatment or to anti-α4β7 treatment respectively. The determination may furthermore comprise assessing risk factors relating to the patient according to known practice in the field. Accordingly in a particular aspect of the invention the method is performed as a prerequisite of additional measures or as an additional test to other assessment protocols to decide on the non-responsive status of the patient. In the present application, the expression "discriminative for non-responsiveness to anti-TNFalpha agent" or "discriminative for non-responsiveness to anti-α4β7 agent" may otherwise be described as a prediction of non-responsiveness or a prediction of resistance to anti-TNFalpha therapy or to anti-α4β7 therapy respectively According to a particular embodiment, the methods of the invention are performed using a IL7R gene and at least one genes in a set of genes selected in the group of FYN, STAT5A, JAK1, CREBBP, PIK3CG, STAT5B, JAK3, ITGA4, PIK3CA, NMI and CRLF2. In a particular embodiment it is performed using a set of genes that comprises at least 2 genes from said group and optionally additional genes not disclosed in said group and preferably genes of the following group: IL2RG, LCK, BCL2, EP300 and TSLP genes; the set may thus encompass 2 to 12 genes (in particular 2 to 8 genes) of said group and optionally 1 or more genes, such as up to 10 or up to 8 genes, outside of said group. Those genes are especially selected in the various groups that have been detailed herein and illustrated in the Examples. The above designated genes are the human genes known in the art and are in particular characterized by their respective sequences available from databases in accordance to the following accession numbers disclosed as gene name/Gene ID(EntrezGene ref)/Accession:
IL7R/3575/NM_002185.4; STAT5A/6776/NM_001288718.1; CREBBP/1387/NM_004380.2; FYN/2534/NM_002037.5; JAK1/3716/NM_002227.3; STAT5B/6777/NM_012448.3; JAK3/3718/NM_000215.3; PIK3CG/5294/NM_002649.3; PIK3CA/5290/NM_006218.3; NMI/9111/NM_004688.2; CRLF2/64109/NM_022148.3; ITGA4/3676/NM_000885.5, IL2RG/3561/NM_000206 (Human Cyc), LCK/3932/NM_005356, BCL2/596/NM_000657.2/NM_000633.2, P300/2033/NM_001429, TSLP/85480/NM_8033035.

In a particular embodiment the method of the invention enables assessing an expression profile wherein the expression profile of a set of genes is determined and said set of genes is a set of 2 to 20 genes in particular a set of 2 to 12 genes, in particular 2 to 12 genes of the above listed group wherein one gene is the IL7R gene.

According to a particular embodiment, the particular group of genes specified as IL7R, FYN, STAT5A, JAK1, CREBBP, PIK3CG, STAT5B, JAK3, ITGA4, PIK3CA, NMI and CRLF2 genes and suitable for performing the method of the invention may be understood as an ordered list from the most preferred or relevant gene (IL7R) for the purpose of the invention, up to the less preferred or relevant one, if considered individually, in particular for the discrimination of the status of the patient that would be the non-responsiveness status. The classification of these genes as an ordered list relies on the results of the analysis involving bioinformatics.

Accordingly, the set of genes suitable to carry out the invention may be designed taking into account this order of preference of said genes for the purpose of the method. In particular the set of genes may contain 2, 3, 4, 5, 6, 7, 8, 9, 10, 11, or 12 genes wherein the selection of genes takes into account the order of appearance of the genes in the list and in particular always comprises the IL7R gene.

In another particular embodiment when it contains less than 9 genes, in particular 2, 3, 4, 5, 6, 7 or 8 genes, including IL7R gene and the set of genes may advantageous be a selection of the genes in the subgroup of FYN, STAT5A, JAK1, CREBBP, PIK3CG STAT5B, and JAK3, with or without consideration of the order of preference in this sublist or, this set of at least 3, 4, 5, 6, 7 or 8 genes comprises at least 2 or at least 3 or at least 4 of the genes in said subgroup. and the additional genes in the remaining less preferred subgroup of ITGA4, PIK3CA, NMI and CRLF2 genes.

Hence according to a particular embodiment, the method of the invention is carrying out wherein the set of genes contains at least 2 genes including IL7R gene and one or more than one gene(s) in the group of JAK1, and STAT5A or in the group of JAK1, STAT5A and JAK3 genes.

In another embodiment, the method of the invention, in particular to discriminate the non-responsiveness status of a patient, is carried out using a set of genes containing at least 2 genes, in particular at least 3 genes, that encompasses the IL7R gene and at least another gene, in particular at least two genes in the group of JAK1, STAT5A, and JAK3 genes, particularly in the group of JAK1 and STAT5A genes.

In particular the set of genes comprises or consists of the IL7R and STAT5A genes, or comprises or consists of the IL7R and JAK1 genes. In another embodiment, the set of genes comprises IL7R and JAK3 genes.

In a particular embodiment the set of genes comprises or consists of IL7R, STAT5A and JAK1 genes. In a preferred embodiment the set of genes comprises or consists of IL7R, STAT5A, JAK1 and JAK3 genes.

In a particular embodiment, the set of genes comprises at least the IL7R gene and 1, 2, 3, 4, 5, 6, 7, 8 or 9 genes of a different subgroup of genes, in particular these additional genes are selected in the group of JAK1, PIC3CA, NMI, CRLF2, IL2RG, LCK, BCL2, EP300 and TSLP, preferably the set includes IL7R and JAK1 genes, together with at least one, especially 1, 2, 3, 4, 5, 6, 7 or 8 of the PIK3CA, NMI, CRLF2, IL2RG, LCK, BCL2, EP300 and TSLP genes.

In a particular embodiment, the set of genes comprises IL7R, JAK1, and comprises additionally 1 to 8 genes in the group of IL2RG, PIK3CA, NMI, CRLF2, LCK, BCL2, EP300 and TSLP genes. In a particular embodiment, the set of genes consists of the group of IL7R, JAK1, IL2RG, PIK3CA, NMI, CRLF2, LCK, BCL2, EP300 and TSLP genes. The inventors have observed that in this set of genes, IL2RG, LCK, BCL2, EP300 and TSLP genes are underexpressed in samples of patients who would be non responsive to treatment with anti-TNFα or possibly to anti-α4β7 agent.

In a particular embodiment, the set of genes comprises IL7R, JAK1, JAK3, STAT5A and additionally comprises 1 to 8 genes in the group of IL2RG, PIK3CA, NMI, CRLF2, LCK, BCL2, EP300 and TSLP genes. In particular, the set of genes comprises IL7R, JAK1, JAK3, STAT5A, IL2RG, PIK3CA, NMI, CRLF2, LCK, BCL2, EP300 and TSLP genes. In particular the set of genes consists of IL7R, JAK1, JAK3, STAT5A, IL2RG, PIK3CA, NMI, CRLF2, LCK, BCL2, EP300 and TSLP genes.

According to the method wherein assessment of the response status, in particular of the usefulness of the treatment is performed, the set of genes preferably comprises or consists of the set of 12 genes disclosed herein. In particular an indication that the patient may benefit from treatment with anti-TNF agent or with anti-α4β7 agent (or otherwise stated would be responsive to the treatment) may be obtained when none of the 12 genes shows an overexpressed expression profile and where the case happens for some of the genes (IL2RG, LCK, BCL2, EP300 and TSLP genes), an underexpression profile with respect to a reference which is illustrative of a healthy standard, optionally in association with results retrieved from assessing other parameters such as clinical signs or risk factors.

The methods of the invention, in particular the method to discriminate the non-responsiveness status of a patient, are carried out in vitro on a biological sample previously obtained from the patient. The sample may be a tissue sample chosen for its capability to reflect the status, especially the inflammation status, caused by the diagnosed condition or disease, in particular when it affects the digestive, especially the gastrointestinal tract. In particular it may be a tissue sample obtained from a biopsie. In a particular embodiment of the invention, the sample is a sample of colon tissue, especially of the colon mucosa or from the skin. In another embodiment, the sample is a body fluid and in particular is a blood sample. The sample may also be a sample of blood cells.

The method of the invention may be applied before the patient has received anti-TNFalpha treatment. In a particular embodiment, the patient is suffering from (especially chronic) condition or disease affecting the digestive tract (in particular relapsing), such as gastrointestinal, in particular intestinal, inflammatory condition or disease or is suffering from a non digestive condition or disease such as cited herein. In particular, the disease or condition is Inflammatory Bowel Disease (IBD), in particular Ulcerative Colitis or Crohn's disease.

Alternatively the method of the invention may be applied after the patient has received anti-TNFalpha treatment. In a particular embodiment, the patient is suffering from (especially chronic) condition or disease affecting the digestive tract (in particular relapsing) such as gastrointestinal, in particular intestinal, inflammatory condition or disease or is suffering from a non digestive condition or disease such as cited herein. In particular, the disease or condition is Inflammatory Bowel Disease (IBD), in particular Ulcerative Colitis or Crohn's disease.

The method of the invention may be applied before the patient has received anti-α4β7 treatment. In a particular embodiment, the patient is suffering from (especially chronic) condition or disease affecting the digestive tract (in particular relapsing), such as gastrointestinal, in particular intestinal, inflammatory condition or disease or is suffering from a non digestive condition or disease such as cited herein. In particular, the disease or condition is Inflammatory Bowel Disease (IBD), in particular Ulcerative Colitis or Crohn's disease.

Alternatively the method of the invention may be applied after the patient has received anti-α4β7 treatment. In a particular embodiment, the patient is suffering from (especially chronic) condition or disease affecting the digestive tract (in particular relapsing) such as gastrointestinal, in particular intestinal, inflammatory condition or disease or is suffering from a non digestive condition or disease such as cited herein. In particular, the disease or condition is Inflammatory Bowel Disease (IBD), in particular Ulcerative Colitis or Crohn's disease.

In an embodiment the invention is directed to a method as defined herein, wherein the step of comparing the gene(s) expression profile to a reference encompasses combining the result in particular the value specific for each gene with the respective result in particular value retrieved from a pre-established reference cohort, in a multivariate analysis.

In another embodiment of the invention, the method of assessing the response status of a patient for a treatment with an anti-TNFalpha agent or with an anti-α4β7 agent, in particular the non-responsiveness status of the patient as described herein comprises a step of comparing the result, in particular the value determined for the gene(s) expression profile to a reference that encompasses comparison with the expression profile of the same gene(s) in a biological sample of a subject healthy for a condition or disease eligible for treatment with anti-TNFalpha agents or with anti-α4β7 agents, in particular inflammatory condition or disease such as Inflammatory Bowel Disease (IBD), in particular Ulcerative Colitis or Crohn's disease or to data equivalent to such expression profile. In a particular embodiment, the patient is suffering from a condition or disease eligible for treatment with anti-TNF agent or with anti-α4β7 agent, in particular chronic (in particular relapsing), such as gastrointestinal, in particular intestinal, inflammatory condition or disease such as Inflammatory Bowel Disease (IBD), in particular Ulcerative Colitis or Crohn's disease. In a particular embodiment, the invention relates to a method of assessing the response status of a patient for a treatment with an anti-TNFalpha agent or with anti-α4β7 agent, in particular the non-responsiveness status of the patient as described herein, wherein determination of the gene(s) expression profile of said one gene or of said set of genes comprises a step of detecting nucleotide targets, preferably mRNA or the nucleic acid, especially DNA resulting from their reverse transcription, wherein each nucleotide target is a nucleic acid resulting from the expression of said one gene or of one of the genes in said set.

According to a particular embodiment, the method of assessing the response status of a patient for a treatment with an anti-TNFalpha agent or with anti-α4β7 agent, in particular the non-responsiveness status of the patient as described herein is a method, wherein the expression profile is detected by dosing cDNA obtained by reverse transcription of the mRNA transcript of the gene(s), optionally after an amplification of said cDNA, such as a by RT-qPCR. Other techniques for the detection may be applied including direct quantification of mRNA trough RNA sequencing or any other direct detection with probes without amplification such as Nanostring.

According to a particular embodiment, the method of assessing the response status of a patient for a treatment with an anti-TNFalpha agent or with anti-α4β7 agent, in particular the non-responsiveness status of the patient as described herein is a method comprising a step of extraction and/or purification of the total RNA of the biological sample. The skilled person knows how to perform such step having recourse to well disclosed techniques in the art.

According to a particular embodiment, the method of assessing the response status of a patient for a treatment with an anti-TNFalpha agent or with anti-α4β7 agent, in particular the non-responsiveness status of the patient as described herein comprises determination of the expression profile of said gene or set of genes wherein the hybridization step of the target nucleic acid is carried out on a solid support or in a liquid medium providing access to probes, especially on an array, in order to recover the expression profile of the gene or of each gene of said set and optionally quantitating said expression profile.

Thus in one of its aspects the invention relates to a reagent comprising or consisting of at least one probe (a probe or a set of probes (provided as separate probes or as a composition of several probes)), wherein said probe(s) is/are suitable and intended to perform the methods of the invention. Each probe is suitable for specific hybridization to the transcript of a gene or to a DNA or cDNA obtained by reverse transcription of such transcript, wherein the gene(s) comprise or consist of genes selected in the group of IL7R, FYN, STAT5A, JAK1, CREBBP, PIK3CG, STAT5B, JAK3, ITGA4, PIK3CA, NMI, CRLF2, IL2RG, LCK, BCL2, EP300 and TSLP genes. The selection of probes suitable for the assessment of the transcript expression of the genes is adapted to the selection of genes in accordance with any of the groups and subgroups defined herein. Particular subgroups all encompass the IL7R gene and are further defined as comprising at least one additional gene within one of the following groups or consist of IL7R and at least one and in particular 2, 3, 4, 5, 6, 7, 8, 9, 10 or 11 genes in the one of following groups:

the group of FYN, STAT5A, JAK1, CREBBP, PIK3CG, STAT5B, JAK3, ITGA4, PIK3CA, NMI and CRLF2 genes, the group of STAT5A, JAK1 and JAK3, and at least one gene in the group of FYN, CREBBP, PIK3CG, STAT5B, ITGA4, PIK3CA, NMI and CRLF2 genes, the group of JAK1, IL2RG, PIK3CA, NMI, CRLF2, LCK, BCL2, EP300 and TSLP genes, the group of JAK1, JAK3, STAT5A, IL2RG, PIK3CA, NMI, CRLF2, LCK, BCL2, EP300 and TSLP genes, the group of JAK1, IL2RG, PIK3CA, NMI, CRLF2, LCK, BCL2, EP300 and TSLP genes and one of both of JAK3 and STAT5A genes.

A probe may accordingly consist in a nucleic acid molecule, preferably a labeled molecule, which specifically matches the targeted gene in the above group of genes and accordingly is capable of hybridizing with a single strand sequence of the gene or more preferably with the sequence of the transcript of the gene or of the reverse transcribed DNA obtained from such transcript, such as cDNA. The probe may thus be a sequence identical or complementary to one strand of the sequence of the gene and may in particular be a fragment of the gene obtained as a reverse transcription DNA of the mRNA transcript of the gene. Probes targeting the genes described herein are available in the art. It is especially disclosed that the following commercial probes which are disclosed as TaqMan gene-expression probes may be used in the context of the methods of the invention.

| IL7R | STAT5A | CREBBP | FYN | JAK1 |
|---|---|---|---|---|
| 3575 | 6776 | 1387 | 2534 | 3716 |
| NM_002185.4 | NM_001288718.1 | NM_004380.2 | NM_002037.5 | NM_002227.3 |
| Hs00902334_m1 | Hs00559637_g1 | Hs00932878_m1 | Hs00176628_m1 | Hs01026983_m1 |
| Hs00902335_m1 | Hs00559648_g1 | Hs00932903_mH | Hs00941608_g1 | Hs01026996_m1 |
| Hs02558840_s1 | Hs00559643_m1 | Hs00932895_m1 | Hs00941603_m1 | Hs01027002_m1 |
| Hs00233682_m1 | Hs00559647_m1 | Hs00932892_g1 | Hs00941607_m1 | Hs01026997_m1 |
| Hs00902338_g1 | Hs00907273_mH | Hs00932875_g1 | Hs00941609_m1 | Hs01026991_m1 |
| Hs03670831_s1 | Hs00559650_mH | Hs00932894_m1 | Hs00941601_m1 | Hs01026985_m1 |
| Hs00904815_m1 | Hs00559638_m1 | Hs00932881_m1 | Hs00941600_m1 | Hs00233820_m1 |
| Hs00904814_m1 | Hs00234181_m1 | Hs00932905_m1 | Hs00941604_m1 | Hs01026992_m1 |
| Hs00902337_m1 | Hs00907274_g1 | Hs00932887_g1 | Hs00941605_m1 | Hs01026994_m1 |
| Hs04406202_m1 | | Hs00932877_m1 | Hs00941614_m1 | Hs01027003_m1 |
| Hs03869842_m1 | | Hs00932880_m1 | Hs00941606_m1 | Hs01026986_m1 |
| Hs03888854_s1 | | Hs00932900_g1 | Hs00941612_m1 | Hs01026995_g1 |
| Hs03869841_m1 | | Hs00231733_m1 | Hs00941615_m1 | Hs01027000_m1 |
| | | Hs00932882_m1 | Hs00941613_m1 | Hs01026993_g1 |

|  |  |  |  |  |
|---|---|---|---|---|
|  |  | Hs00932879_m1 | Hs00941611_m1 | Hs01026987_g1 |
|  |  | Hs00932901_m1 | Hs00942468_m1 | Hs01026989_g1 |
|  |  | Hs00932876_g1 |  | Hs01026999_m1 |
|  |  | Hs00932896_m1 |  | Hs01026998_m1 |
|  |  | Hs00932904_m1 |  | Hs01026984_m1 |
|  |  | Hs00932899_m1 |  | Hs01026990_m1 |
|  |  | Hs00932902_g1 |  | Hs01027001_m1 |
|  |  | Hs00932883_m1 |  | Hs01026988_m1 |
|  |  | Hs00932897_m1 |  | Hs01038649_m1 |
|  |  | Hs00932898_m1 |  |  |

| STAT5B | JAK3 | PIK3CG | PIK3CA | NMI |
|---|---|---|---|---|
| 6777 | 3718 | 5294 | 5290 | 9111 |
| NM_012448.3 | NM_000215.3 | NM_002649.3 | NM_006218.3 | NM_004688.2 |
| Hs00560026_m1 | Hs00354555_m1 | Hs00932390_m1 | Hs00907957_m1 | Hs00190768_m1 |
| Hs00560035_m1 | Hs01006628_g1 | Hs00277090_m1 | Hs00907950_m1 | Hs01040298_m1 |
| Hs00273500_m1 | Hs00354563_g1 | Hs00932393_m1 | Hs00907966_m1 | Hs01040300_m1 |
| Hs00957780_gH | Hs00354564_m1 | Hs00932389_g1 | Hs00907954_m1 | Hs01040301_g1 |
| Hs00957781_m1 | Hs01006616_m1 | Hs00932391_m1 | Hs00907951_m1 | Hs01040299_m1 |
| Hs00957782_m1 | Hs01006621_g1 | Hs00932394_m1 | Hs00907963_g1 | Hs01040297_m1 |
| Hs00957777_g1 | Hs01006626_g1 | Hs00176916_m1 | Hs00907955_g1 |  |
|  | Hs01006624_g1 | Hs00936114_m1 | Hs00907961_m1 |  |
|  | Hs01006629_g1 | Hs00907960_m1 |  |  |
|  | Hs01006627_g1 | Hs00180679_m1 |  |  |
|  | Hs01006618_g1 | Hs00907948_g1 |  |  |
|  | Hs01006625_g1 | Hs00907965_m1 |  |  |
|  | Hs01006630_g1 | Hs00907958_g1 |  |  |
|  | Hs01006615_m1 | Hs00907959_m1 |  |  |
|  | Hs00169663_m1 | Hs00907956_g1 |  |  |
|  | Hs01006622_m1 | Hs00907964_g1 |  |  |
|  | Hs01006617_g1 | Hs00611502_s1 |  |  |
|  |  | Hs00907953_m1 |  |  |
|  |  | Hs00907952_g1 |  |  |
|  |  | Hs03828550_s1 |  |  |

|  | CRLF2 |  | ITGA4 |  |
|---|---|---|---|---|
|  | 64109 |  | 3676 |  |
|  | NM_022148.3 |  | NM_000885.5 |  |
|  | Hs00845692_m1 |  | Hs00168433_m1 |  |
|  | Hs00913509_s1 |  | Hs01047121_g1 |  |
|  | Hs04405174_m1 |  | Hs01051578_g1 |  |
|  |  |  | Hs01047103_m1 |  |
|  |  |  | Hs01047105_g1 |  |
|  |  |  | Hs01047117_m1 |  |
|  |  |  | Hs01047123_m1 |  |
|  |  |  | Hs01047124_m1 |  |
|  |  |  | Hs01047106_g1 |  |
|  |  |  | Hs01047122_m1 |  |
|  |  |  | Hs01047118_m1 |  |
|  |  |  | Hs01047109_m1 |  |
|  |  |  | Hs01047127_m1 |  |
|  |  |  | Hs01047110_m1 |  |
|  |  |  | Hs01047119_g1 |  |
|  |  |  | Hs01047107_m1 |  |
|  |  |  | Hs01047111_m1 |  |
|  |  |  | Hs01047108_m1 |  |
|  |  |  | Hs01047104_m1 |  |
|  |  |  | Hs01047114_m1 |  |
|  |  |  | Hs01047126_g1 |  |
|  |  |  | Hs01047113_m1 |  |

The invention also concerns a solid support, especially an array, comprising at least one probe (a probe or a set of probes) wherein each probe is suitable for hybridization to the transcript of a gene of the set of genes wherein said set comprises or consists of genes selected in the group of IL7R, FYN, STAT5A, JAK1, CREBBP, PIK3CG, STAT5B, JAK3, ITGA4, PIK3CA, NMI, CRLF2, IL2RG, LCK, BCL2, EP300 and TSLP genes, in particular selected according to the herein described embodiments for the set of genes. Each probe is linked to the support in conditions suitable to carry out the method of the invention. Alternatively said probe is suitable for hybridization to the DNA obtained by reverse transcription of the mRNA transcript of a gene of the set of genes as defined herein. The solid support may in particular comprise probes suitable for hybridization to the transcript of the IL7R gene and furthermore to the transcript of at least one, especially of each gene of one the following sets of genes:

the group of FYN, STAT5A, JAK1, CREBBP, PIK3CG, STAT5B, JAK3, ITGA4, PIK3CA, NMI and CRLF2 genes, the group of STAT5A, JAK1 and JAK3, and at least one gene in the group of FYN, CREBBP, PIK3CG, STAT5B, ITGA4, PIK3CA, NMI and CRLF2 genes, the group of JAK1, IL2RG, PIK3CA, NMI, CRLF2, LCK, BCL2, EP300 and TSLP genes, the group of JAK1, JAK3, STAT5A, IL2RG, PIK3CA, NMI, CRLF2, LCK, BCL2, EP300 and TSLP genes, the group of JAK1, IL2RG, PIK3CA, NMI, CRLF2, LCK, BCL2, EP300 and TSLP genes and one of both of JAK3 and STAT5A genes.

Particular subgroups for the definition of probes thus all encompass the IL7R gene and are further defined as comprising at least one additional gene within one of said groups or consist of IL7R and at least one and in particular 2, 3, 4, 5, 6, 7, 8, 9, 10 or 11 genes in the said groups.

In a further aspect, the invention relates to a probe or a set of probes wherein each probe is suitable for hybridization to the transcript of a gene selected in the group of IL7R, FYN, STAT5A, JAK1, CREBBP, PIK3CG, STAT5B, JAK3, ITGA4, PIK3CA, NMI CRLF2, IL2RG, LCK, BCL2, EP300 and TSLP genes, in particular selected according to the herein described embodiments for the set of genes, in a solution in conditions suitable to carry out the method of the invention. Alternatively said probe is suitable for hybridization to the DNA obtained by reverse transcription of the mRNA transcript of a gene of the set of genes as defined herein. Probes may in particular be provided for hybridization to the transcript of the IL7R gene and to the transcript of at least one gene and especially each gene of one of the following groups:

the group of FYN, STAT5A, JAK1, CREBBP, PIK3CG, STAT5B, JAK3, ITGA4, PIK3CA, NMI and CRLF2 genes, the group of STAT5A, JAK1 and JAK3, and at least one gene in the group of FYN, CREBBP, PIK3CG, STAT5B, ITGA4, PIK3CA, NMI and CRLF2 genes, the group of JAK1, IL2RG, PIK3CA, NMI, CRLF2, LCK, BCL2, EP300 and TSLP genes, the group of JAK1, JAK3, STAT5A, IL2RG, PIK3CA, NMI, CRLF2, LCK, BCL2, EP300 and TSLP genes, the group of JAK1, IL2RG, PIK3CA, NMI, CRLF2, LCK, BCL2, EP300 and TSLP genes and one of both of JAK3 and STAT5A genes.

Particular subgroups for the definition of probes thus all encompass the IL7R gene and are further defined as comprising at least one additional gene within one of said groups or consist of IL7R and at least one and in particular 2, 3, 4, 5, 6, 7, 8, 9, 10 or 11 genes in the said groups.

Of course the set of probes is necessarily adapted to the set of genes selected in order to perform the method of the invention and therefore the definitions of the various embodiments related to the set of genes apply to the definition of the set of probes.

The invention also relates to a kit comprising a probe or a set of probes as defined herein, and reagents necessary for hybridization of said probe(s) to a nucleic acid target in a biological sample.

According to another embodiment the invention relates to a method of assessing the response status of a patient for a treatment with an anti-TNFalpha agent or with anti-α4β7 agent, in particular the non-responsiveness status of the patient as described herein wherein determination of the gene(s) expression profile of said one gene or of said set of genes comprises a step of detecting the proteins expressed by said gene(s). A reagent suitable to perform such protein includes antibodies or fragments thereof wherein each antibody specifically binds to one of said proteins.

Methods for the detection of proteins are well known from the person skilled in the art and as examples encompass immunoassays e.g., ELISA, RIA (radioimmunoassay), IEA (immunoenzyme assay), Western-Blot, Mass-spectrometry, immunohistology and the like or encompass any method assaying functional activity relative to the encoded proteins e.g., biological activity measurement.

Accordingly, means for the detection of proteins encoded by one gene or a set of genes comprise a set of antibodies or fragments thereof (as separate antibodies or as a composition of antibodies) wherein each antibody specifically binds a protein expressed by one gene selected in the group of IL7R, FYN, STAT5A, JAK1, CREBBP, PIK3CG, STAT5B, JAK3, ITGA4, PIK3CA, NMI, CRLF2, IL2RG, LCK, BCL2, EP300 and TSLP genes. The set or the composition of antibodies is of course adapted to the set of genes the expression profile of which is assessed. In particular in the set of antibodies, an antibody specifically binds to the IL7R protein and additional antibodies are provided wherein each antibody specifically binds a protein expressed by one gene, especially each gene in the following groups:

the group of FYN, STAT5A, JAK1, CREBBP, PIK3CG, STAT5B, JAK3, ITGA4, PIK3CA, NMI and CRLF2 genes, the group of STAT5A, JAK1 and JAK3, and at least one gene in the group of FYN, CREBBP, PIK3CG, STAT5B, ITGA4, PIK3CA, NMI and CRLF2 genes the group of JAK1, IL2RG, PIK3CA, NMI, CRLF2, LCK, BCL2, EP300 and TSLP genes the group of JAK1, JAK3, STAT5A, IL2RG, PIK3CA, NMI, CRLF2, LCK, BCL2, EP300 and TSLP genes the group of JAK1, IL2RG, PIK3CA, NMI, CRLF2, LCK, BCL2, EP300 and TSLP genes and one of both of JAK3 and STAT5A genes.

Particular subgroups for the definition of the antibodies thus all encompass antibodies that specifically binds the protein encoded by the IL7R gene and are further defined as comprising at least one antibody that specifically binds to an additional gene within one of said groups or consist of antibodies that specifically bund IL7R and at least one antibody in particular 2, 3, 4, 5, 6, 7, 8, 9, 10 or 11 different antibodies (with respect to their binding properties) wherein each binds specifically to one protein expressed by one gene in the said groups.

Each antibody (or fragment thereof) may be linked to a support in conditions suitable to carry out the method of the invention. Alternatively the antibody(ies) (or fragments thereof) may be provided in a solution to perform the method of the invention.

The invention also relates to a kit comprising an antibody or a set of antibodies as defined herein, and reagents necessary to enable the immune recognition between the antibodies and the proteins in a biological sample.

The invention also concerns a solid support, especially an array or a solution, comprising at least one antibody or fragment thereof (an antibody (or fragments thereof) or a set of antibodies (or fragments thereof)), wherein each antibody is suitable for specifically binding to the protein expressed from the transcript of a gene of the set of genes wherein said set comprises or consists of genes selected in the group of IL7R, FYN, STAT5A, JAK1, CREBBP, PIK3CG, STAT5B, JAK3, ITGA4, PIK3CA, NMI CRLF2, IL2RG, LCK, BCL2, EP300 and TSLP genes, in particular selected according to the herein described embodiments for the set of genes. Each antibody is linked to the support in conditions suitable to carry out the method of the invention or is present in a solution.

In a further aspect, the invention relates to a reagent comprising at least one antibody (or fragments thereof) or a set of antibodies (or fragments thereof) wherein each antibody is suitable for binding to the protein expressed from the transcript of a gene selected in the group of IL7R, FYN, STAT5A, JAK1, CREBBP, PIK3CG, STAT5B, JAK3, ITGA4, PIK3CA, NMI CRLF2 IL2RG, LCK, BCL2, EP300 and TSLP genes, in particular selected according to the herein described embodiments for the set of genes, in a solution in conditions suitable to carry out the method of the invention. Again the particular groups of genes all comprise the IL7R gene and at least one gene, especially each gene in in a group that may be selected among:

- the group of FYN, STAT5A, JAK1, CREBBP, PIK3CG, STAT5B, JAK3, ITGA4, PIK3CA, NMI and CRLF2 genes,
- the group of STAT5A, JAK1 and JAK3, and at least one gene in the group of FYN, CREBBP, PIK3CG, STAT5B, ITGA4, PIK3CA, NMI and CRLF2 genes
- the group of JAK1, IL2RG, PIK3CA, NMI, CRLF2, LCK, BCL2, EP300 and TSLP genes
- the group of JAK1, JAK3, STAT5A, IL2RG, PIK3CA, NMI, CRLF2, LCK, BCL2, EP300 and TSLP genes
- the group of JAK1, IL2RG, PIK3CA, NMI, CRLF2, LCK, BCL2, EP300 and TSLP genes and one of both of JAK3 and STAT5A genes.

Particular subgroups of genes for the definition of antibodies binding to the proteins expressed by the transcripts of these genes thus all encompass the IL7R gene and are further defined as comprising at least one additional gene within one of said groups or consist of IL7R and at least one and in particular 2, 3, 4, 5, 6, 7, 8, 9, 10 or 11 genes in the said groups.

Of course the set of antibodies or fragments thereof is necessarily adapted to the set of genes selected in order to perform the method of the invention and therefore the definitions of the various embodiments related to the set of genes apply to the definition of the set of antibodies or fragments thereof.

The invention also relates to a kit comprising an antibody or a set of antibodies as defined herein, and reagents necessary to carry out the immunological reaction with proteins expressed from the target gene(s) contained in a biological sample.

Furthermore, in one aspect the invention relates to the use of means for the determination of the level of expression profile of genes, in particular a set of probes, a set of antibodies, solid support, arrays, reagents, solutions or kits as defined herein and especially above which comprises said probes or said antibodies (or fragments thereof), to determine the expression profile of a gene or a set of genes selected in the group of IL7R, FYN, STAT5A, JAK1, CREBBP, PIK3CG, STAT5B, JAK3, ITGA4, PIK3CA, NMI CRLF2 IL2RG, LCK, BCL2, EP300 and TSLP genes, in a biological sample obtained from a human patient suffering from a condition or disease which is eligible for treatment with anti-TNFalpha agent or with anti-α4β7 agent, in particular who is assessed for the usefulness of a treatment with an anti-TNFalpha agent or with anti-α4β7 agent, in particular for non-responsiveness to anti-TNFalpha agent or to anti-α4β7 agent. In a particular embodiment, the patient is suffering from (in particular chronic and/or relapsing) an inflammatory condition or disease, particularly an inflammatory condition or disease of the digestive tract, more particularly a gastrointestinal inflammatory condition or disease, and even more particularly intestinal inflammatory condition or disease such as Inflammatory Bowel Disease (IBD), in particular Ulcerative Colitis or Crohn's disease.

Each and every embodiment disclosed herein in relation to the definition of the set of genes when disclosing the method similarly applies to the definition of the set of probes or set of antibodies (or fragments thereof), compositions comprising probes or antibodies, and to the definition of the support, arrays, solution and kit comprising the probes or the antibodies (or fragments thereof) and also applies to the use defined herein.

The invention also concerns a method according to the definitions provided herein for the assessment of the response status of a patient who suffers from a condition or disease eligible for treatment with anti-TNF agents or with anti-α4β7 agent according to the various embodiments disclosed herein, wherein determination of the expression profile of said gene or set of genes comprises

- a hybridization step to target nucleic acid transcribed or reverse transcribed from the genes, such as one performed on a solid support or in liquid medium providing probes, especially on an array, prior to a step of recovering the expression profile of each gene of said set and optionally quantitating said expression profile or,
- a binding step to proteins expressed by the genes wherein said binding is performed on solid support or in liquid medium providing the antibodies or fragments thereof, especially on an array, prior to a step of recovering the expression profile of each gene of said set and optionally quantitating said expression profile.

The invention also relates to an anti-TNF agent or to a anti-α4β7 agent for use in the treatment of a disease or condition eligible for treatment with anti-TNF agents or with anti-α4β7 agent, in particular an inflammatory condition or disease, particularly of the digestive tract, more particularly a gastrointestinal inflammatory condition or disease and even more particularly a intestinal inflammatory condition or disease, such as Inflammatory Bowel Disease (IBD), in particular Ulcerative Colitis or Crohn's disease wherein the patient has been assessed by a method as disclosed herein and as a result has been regarded as responsive to the treatment with anti-TNF agent or with anti-α4β7 agent.

Further characteristics and advantages of the invention may be apparent from the Examples below and from the figures.

LEGEND OF THE FIGURES

FIG. 1: Meta-analysis of IL-7R signaling signature in colon biopsies before initiation of anti-TNF therapy using the 3 cohorts (GSE16879-CD, GSE16879-UC and GSE1225-UC) with anti-TNF response defined by complete histological mucosal healing.

(a) Heatmap of the expression of the 20 selected genes previously reported as key members of the IL-7R signaling pathway[38], in colon biopsies of responders (black, n=32) and non-responders (grey, n=33) before anti-TNF therapy. Meta-analysis of 3 UC and cCD cohorts with histological healing as the anti-TNF response criteria: dataset GSE16879[44] and GSE12251[43]. The heat map represents median centered colorized expression values in which yellow values indicate over-expression and blue values indicate under-expression. (b) PCA (Principal Component Analysis) from the meta-dataset at week 0 of the IL-7R signaling signature (20 selected genes), in the same group of patients as in (a). (c) The meta-analysis identified 12 significantly over-expressed genes between responders and non-responders, among which 4 genes (IL7R, JAK1, JAK3, STAT5A) were significantly associated in a multivariate analysis. (d) ROC analysis of IL7R, STAT5A, JAK1 and JAK3 expression (e) ROC analysis of IL7R expression, the 4-genes IL7R-related signature discriminating anti-TNFalpha response in the meta-analysis (IL7R, STAT5A, JAK1 and JAK3) and the 4-genes IL7R-related signature minus IL7R expression. (f) ROC analysis of the 4-genes IL7R-related signature minus IL7R expression, or minus JAK3 expression, or minus JAK1 expression, or minus STAT5A expression. (g) ROC analysis of IL7R and JAK3 or JAK1 or STAT5A expression.

Figure 2:
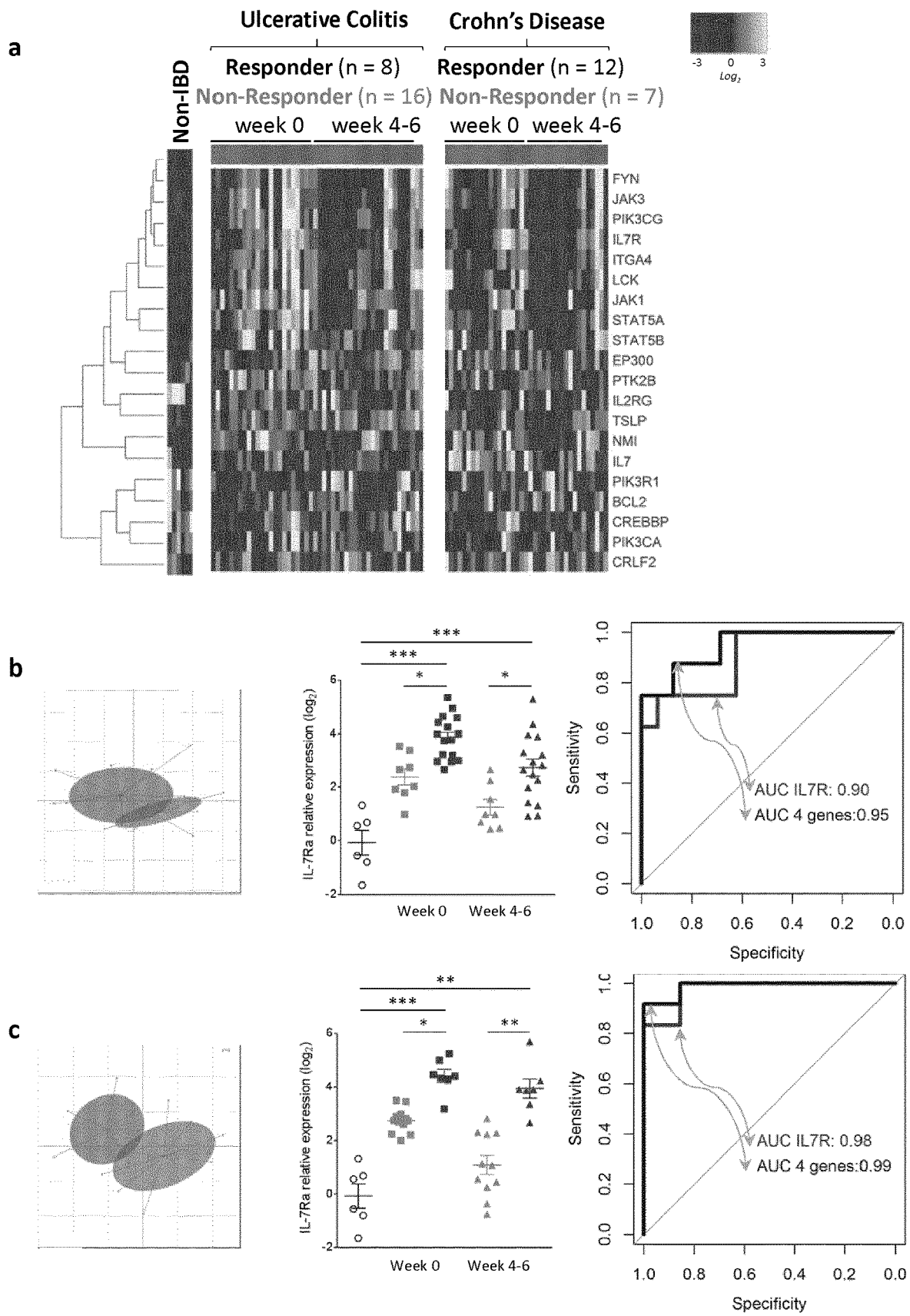
Figure 2:
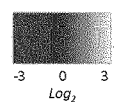
Figure 2:
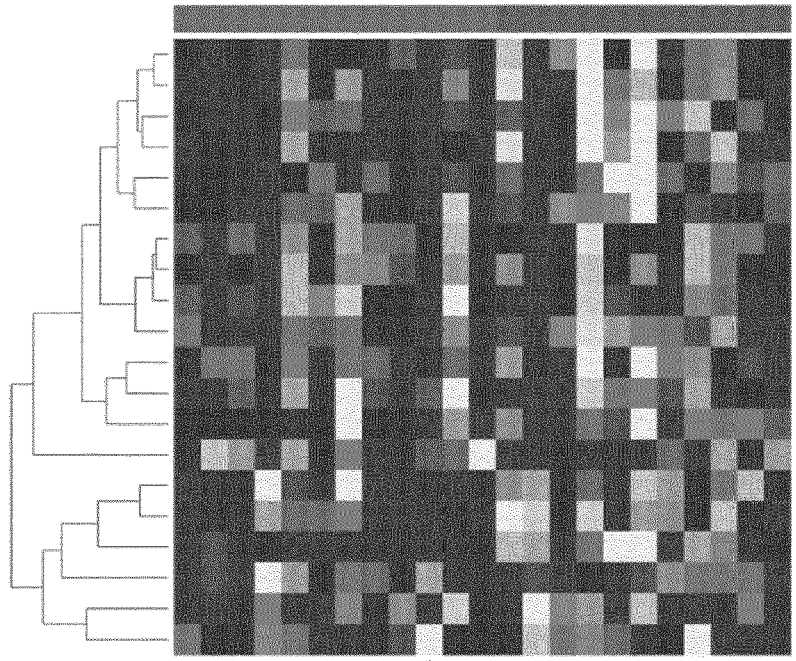
Figure 2:
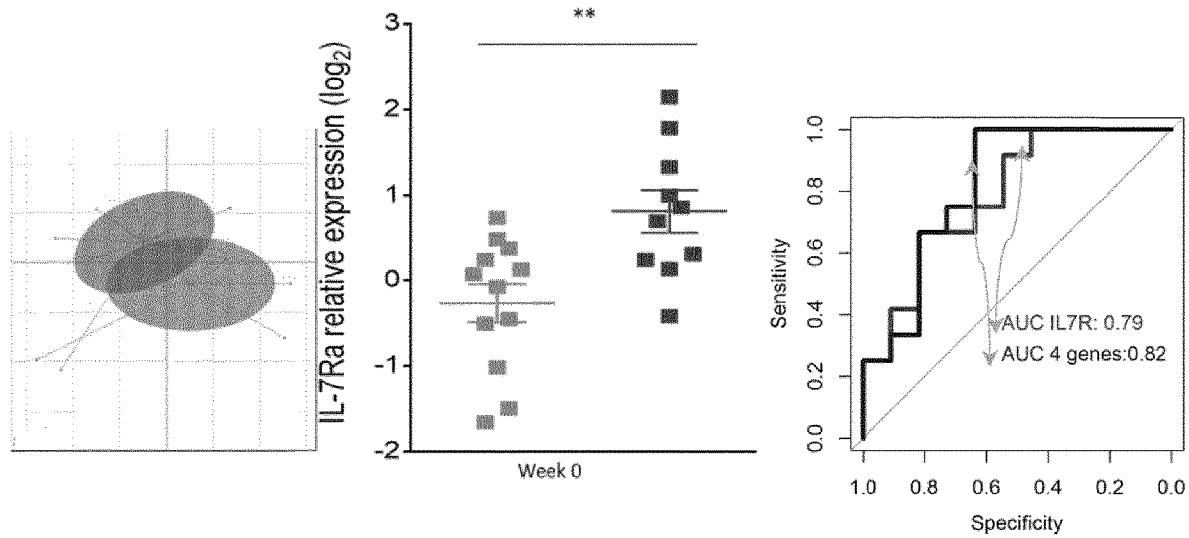

FIG. 2: Colonic mucosal IL7R and IL-7R signaling pathway expression at baseline is associated with response to anti-TNFα therapy.
(a) Heatmap of the 20 selected genes previously reported as key members of the IL-7R signaling pathway[38], in colon biopsies from non-IBD controls (black: n=6), UC patients (black: responder n=8, grey: non-responder n=16) and CD patients (grey: responder n=12, black: non-responder n=7) treated with anti-TNFα therapy (dataset GSE16879[44]). Samples were analyzed within a week before anti-TNFα infusion and 4-6 weeks after treatment initiation. The heatmap represents median-centered and colorized expression values in which light grey up to white and dark grey up to black values indicate over-expression and under-expression, respectively. (b) UC and (c) CD cohort analysis using same group of patients as in (a): Left-PCA at week 0 of the IL-7R signaling signature, Middle-Relative IL7R expression before and after anti-TNFα treatment (log 2 data normalized to control median), and Right-ROC (Receiver Operating Characteristic) analysis of IL7R expression and the 4-gene IL7R-related signaling signature distinguishing anti-TNFα responders and non-responders in this dataset (i.e. IL7R, JAK3, JAK1 and STAT5). (d) Heatmap of the IL-7R signaling signature (20 selected genes) in colon biopsies from UC patients (black: responder n=12, grey: non-responder n=10) before treatment with anti-TNF therapy (dataset GSE12251[43]). (e) Left-PCA at week 0 of the IL-7R signaling signature, Middle-Relative IL7R expression before anti-TNF treatment (log 2 data normalized to median of responders), and Right-ROC analysis of IL7R expression and the 4-gene IL7R-related signature distinguishing anti-TNF responders and non-responders in this dataset (i.e. IL7R, JAK3, JAK1 and STAT5). *p<0.05; p<0.01; *p<0.001 between indicated groups.

Figure 3:
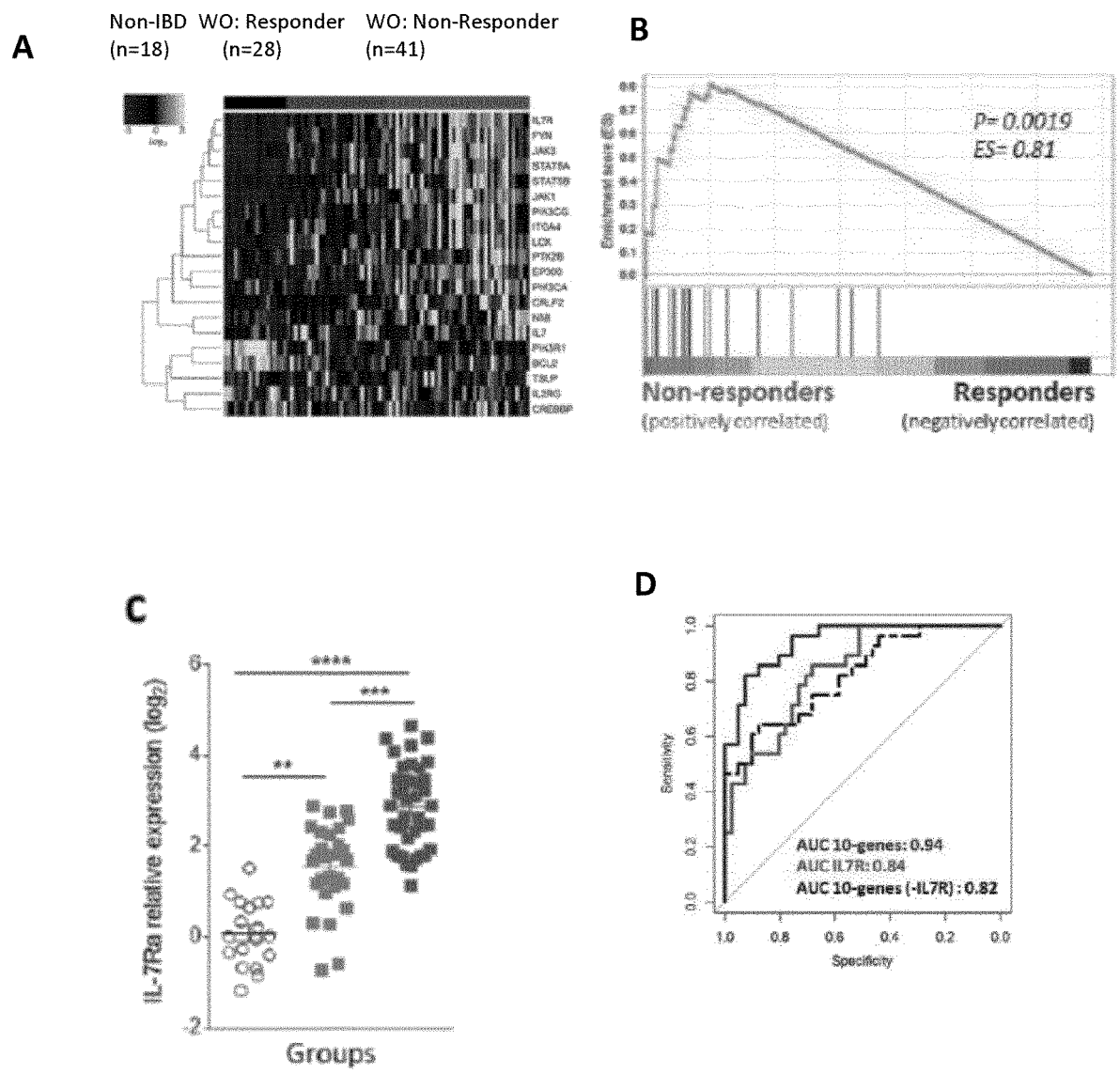

FIG. 3: Colonic mucosal IL7R and IL7R signaling pathway expression at baseline is associated with non-response to anti-TNF therapy.
(a) Heatmap of the expression of the 20 selected genes previously reported as key members of the IL7R signaling pathway(39), in colon biopsies of non-IBD controls (n=18), responders (center, n=28) and non-responders (right, n=41) before anti-TNF therapy. Meta-analysis of 3 UC cohorts with histological healing as the anti-TNF response criteria: dataset GSE16879(45) and GSE12251(44), and GSE73661 (46). The heat map represents median centered colorized expression values in which light grey (yellow) values indicate over-expression and dark grey (blue) values indicate under-expression. (b) Gene set enrichment analysis from the meta-dataset at week 0 of the IL7R signaling signature (20 selected genes). (c) Relative IL7R expression before anti-TNF treatment (log 2 data normalized to control median) in the same group of patients as in (a). (d) ROC analysis of IL7R, IL7R 10-gene signature (IL7R, IL2RG, JAK1, PIK3CA, LCK, BCL2, EP300, NMI, CRLF2 and TSLP) and the signature without IL7R (9 genes) expression distinguishing anti-TNF responders and non-responders. p<0.01; *p<0.001 and ****p<0.0001 between indicated groups using Kruskal-Wallis test with Dunn's ad post-hoc test.

Figure 4:
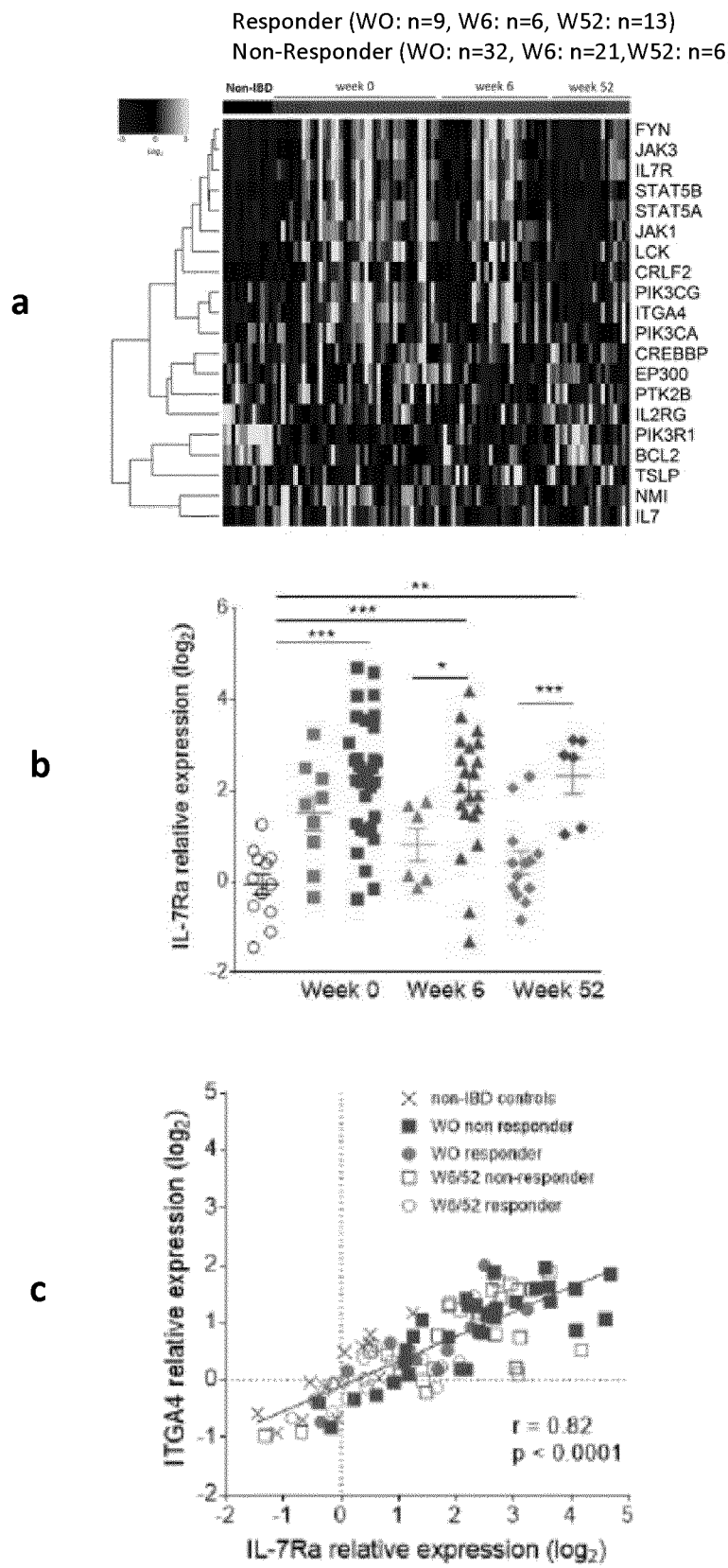

FIG. 4: IL7R signaling signature in colon bioposies before and after anti-α4β7 (Vedolizumab) therapy in UC patients.
(a) Heatmap of the 20 selected genes previously reported as key members of the IL7R signaling pathway[39], in colon biopsies from non-IBD controls (first in the left part (black): n=12) and UC patients (second from the left part (green): responder n=9-13, third from the left part (red): non-responder n=6-31) treated with anti-α4β7 therapy (dataset GSE73661[46]). Samples were analyzed before anti-α4β7 infusion as well as 6 or 52 weeks after treatment initiation. The heatmap represents median-centered and colorized expression values in which light grey (yellow) and dark grey (blue) values indicate over-expression and under-expression, respectively. (b) Relative IL7R expression before and after anti-α4β7 treatment (log 2 data normalized to control median). (c) Correlative analysis between IL7R and ITGA4 relative gene expression before anti-α4β7 treatment (log 2 data normalized to control median) in colon mucosa of UC patients and non-IBD controls. *p<0.05; p<0.01; **p<0.001 between indicated groups.

EXAMPLES

Signaling networks perpetuating chronic gastrointestinal inflammation in Crohn's disease (CD) and ulcerative colitis (UC), the two main forms of inflammatory bowel diseases (IBD), remain unclear in man. According to an analysis of nearly 500 patients with IBD and 100 controls, we report here that key transcripts of the IL-7 receptor (IL-7R) pathway accumulate in inflamed colon tissues of severe IBD patients not responding to either immunosuppressive/corticosteroids or anti-TNFα therapies. High expression of both IL-7R and IL-7R signaling signature transcripts in the colon before treatment are strongly associated with nonresponsiveness to anti-TNFα therapy. While in mice IL-7 is known to play a role in systemic inflammation, we found that in humans IL7R and IL-7R-signaling signature locally accumulate in diseased tissues, particularly in refractory diseases and non-responders patients to the gold standard of treatment constituted by anti-TNF therapy.

INTRODUCTION

Inflammatory bowel disease (IBD) consists of two major forms, ulcerative colitis (UC) and Crohn's disease (CD), which are chronic relapsing gastrointestinal disorders characterized by chronic intestinal inflammation, dysregulated immune responses to intestinal microbiota and dysfunction of the epithelial barrier[1,2]. The incidence and prevalence of IBD is increasing worldwide and these diseases are associated with marked morbidity and have a major impact on quality of life and ability to work[3,4]. Current conventional treatments are aimed at dampening inflammation with the gradual use of anti-inflammatory agents, steroids, immunosuppressive drugs and biological agents targeting inflammatory cytokines (mainly tumor necrosis factor alpha (TNFα)) for refractory and severe forms of IBD[5,6]. However, approximately one-third of patients receiving anti-TNFα agents do not respond to treatment (primary failure), and a significant proportion (up to 50%) become refractory over time (secondary failure)[7]. A key feature of IBD is also the rapid recruitment and prolonged persistence of leukocytes at the site of inflammation, which is facilitated by integrin interaction with cognate receptors expressed by endothelial cells allowing cell adhesion and transmigration[8,9]. Emerging therapies are targeting this entry point to the gut with anti-adhesion molecules, specially targeting the gut-specific α4β7 integrin[10,11]. However, these therapies do not induce remission in more than half of patients and relapse also occurs over time in primary responders. Thus, one major goal is to identify novel mechanisms and signaling networks which underly the chronicity and relapse of IBD.

Interleukin-7 (IL-7) is a limiting and non-redundant cytokine produced mainly by epithelial and stromal cells which regulates T-lymphocytes homeostasis[12,13]. Almost all conventional mature T lymphocytes express high IL-7 receptor (IL-7R) levels, with the specific exception of naturally-occurring regulatory T-cells (Tregs), constituting a rare opportunity to selectively target pathogenic effectors while preserving natural regulators[14-16]. IL-7 signals through the cell surface IL-7R that consists of a specific IL-7R alpha chain (IL-7Rα, CD127) which dimerizes with the common cytokine receptor gamma chain (γc, CD132, IL2RG)[17]. Upon activation, IL-7R delivers proliferative and anti-apoptotic signals by activating phosphoinositide 3-kinase (PI3K) and Janus kinase-signal transducer and activator of transcription (JAK-STAT) pathways as well as regulating expression of anti- and pro-apoptotic BCL-2 family members[18]. More than two decades of research have reproducibly highlighted the crucial systemic influence of the IL-7 pathway and depicted IL-7 as a fuel for chronic autoimmune and inflammatory diseases as well as transplant rejection in diverse rodents models[19,20]. Remarkably, the colon is the major source of IL-7 outside of the lymphoid tissues in mice and commensal microflora promotes steady-state IL-7 production by intestinal epithelial cells[21,22]. IL-7 transgenic mice spontaneously developed chronic colitis with IL-7Rα[high] T cells infiltrating the gut mucosa which, once isolated, transferred colitis to immunodeficient recipient mice, thereby demonstrating their pathogenicity[23-27]. More recently, IL-7Rα[high] innate lymphoid cells (ILCs) were described as new key effectors of IBD[28-30], and IL-7Rα antagonists both suppressed adaptive and innate inflammatory responses in different experimental models of colitis[24,25,31,32].

In humans however, research on IBD has mainly focused on a pro-inflammatory and anti-inflammatory cytokine balance[33-35] while the IL-7/IL-7Rα axis remains poorly studied. IL-7 production by intestinal epithelial cells and IL-7Rα expression by mucosal T lymphocytes were described in colon biopsies from healthy donors[36]. One study reported genetic loci variation of the IL-7Rα gene being associated with susceptibility to UC[37]. Lastly, elevated IL-7 signaling pathway gene expression in blood CD8 T cells at diagnosis was significantly associated with relapsing and a more aggressive IBD disease course[38]. Whether IL-7 activities are implicated in the pathogenesis of IBD in humans and determines the fate of treatment is unknown.

Results

Colon-Specific Increased Mucosal IL-7R Signaling Pathway Signature in Refractory IBD Higher gene expression of the IL-7 signaling pathway members in peripheral blood CD8+ T cells has been previously correlated with a relapsing and aggressive disease course of IBD[38]. We therefore sought to address whether the local/mucosal IL-7/IL-7R pathway could be enriched in severe IBD and associated with the failure to conventional therapies. For this purpose, we analyzed the transcriptional IL-7/IL-7R signaling signature (20 genes curated from BioCarta by the Molecular Signatures database[38]) in colon mucosal biopsies from previously published cohorts of IBD patients with clinically active or inactive disease after immunosuppressive therapy. We examined two independent cohorts (UC (n=23) compared to controls without IBD (n=13)[39] and UC (n=97) or Crohn's disease (n=8) compared to controls without IBD (n=11)[40]). We found this 20 mRNA expression signature allows clustering of samples according to the clinical status (FIG. 1a and FIG. 3a) with a particularly significant accumulation of IL-7Rα mRNA (IL7R) transcripts in inflamed mucosa from refractory IBD patients relative to those in uninvolved control mucosa from same patients (P<0.0001), mucosa from responder patients (P<0.001) or non-IBD controls. Principal Component Analysis (PCA) of the mucosal IL-7R signaling signature after immunosuppressive therapy displayed in both cohorts, a clear and distinct separation between active versus inactive disease status and the group of uninvolved mucosa which gathered with non-IBD controls.

Similarly, the IL-7R signaling signature after anti-TNFα treatment allows to distinguish between biopsies according to disease status in a third cohort of UC patients involved in the phase 3 ACT-1 clinical trial of Infliximab (including long-term responders (n=17), short-term responders and then relapse (n=8) and primary non-responders (n=6)[41]). PCA of the mucosal IL-7R signature clearly separates responders from non-responder patients 30 weeks after maintenance with anti-TNFα treatment. Furthermore, mucosal IL7R expression is significantly higher in clinically active versus inactive disease in anti-TNFα treated-patients both at early (week 8, P<0.05)) and late (week 30, P<0.001) time-points. IL7R expression significantly decreased after anti-TNF therapy in long-term responders compared to baseline pre-treatment levels (P<0.001), however no significant difference was measurable before treatment between groups in this clinical trial cohorts In contrast to colon mucosa, the IL7R signature in ileal biopsies is not associated with clinical status in a fourth cohort(43) of untreated pediatric patients with newly diagnosed ileal (iCD, n=143) or colon-only (cCD, n=30) Crohn's disease or ulcerative colitis (n=38) as compared to pediatric healthy controls (n=42). IL7R expression is only higher in ileal biopsies with histological micro-inflammation versus uninflamed biopsies of cCD, however no difference is observed in ulcerated or non-ulcerated iCD relative to healthy controls. Furthermore, IL7R is not differentially expressed in colon mucosa of different non-IBD type of controls, including in inflammatory non-IBD pathology such as diverticulitis (Data not shown). Altogether, the data indicate that mucosal expression of the IL7R signaling pathway, and specifically IL7R, are strongly and selectively associated with colon but not ileal IBD inflammation. Expression is related to disease activity in IBD patients (Table 1) and could be one mechanism associated with refractory and severe IBD.

Colonic IL-7Rα Expression Predicts Resistance to Anti-TNFα Therapy

We then asked whether the mucosal IL-7R signaling signature is associated with responsiveness to anti-TNFα before initiation of biologic therapy in patients refractory to corticosteroids and/or immunosuppression. We thus performed a meta-analysis of publically available transcriptional datasets of three cohorts of UC and cCD patients with colon mucosa biopsies performed before anti-TNFα treatment (within a week)[43,44]. In these three cohorts, anti-TNFα response was defined as histological healing analyzed 4-6 weeks after their first anti-TNFα infusion (altogether: n=33 non-responders versus n=32 responders). This meta-analysis revealed that the IL-7R signaling signature is already elevated in colon biopsies of primary IBD non-responder patients before initiation of anti-TNFα therapy and differs between responders and non-responders according to a Principal Component Analysis (PCA) (FIG. 1 a and b). Within the IL-7R signature, 12 genes were identified as significantly up-regulated in non-responders before treatment, with IL7R being the highest (FC=3.01, adjusted p.value=<0.000001). In a multivariate analysis, four other genes (IL7R, JAK1, JAK3, STAT5A) were significantly associated with unresponsiveness to anti-TNFα (FIG. 1-c). Finally, individual pretreatment expression of IL7R and of the 4 IL-7R-restricted gene signature strongly discriminates primary nonresponsiveness to anti-TNFα therapy in this meta-analysis (IL7R ROC AUC=86% with 95% CI: 0.77-0.95, 4-genes IL-7R signature ROC AUC=92% with 95% CI: 0.85-0.99) (FIG. 1 d-g).

Analysis within each cohort independently, showed that pretreatment individual baseline IL7R expression is significantly increased in UC and cCD non-responder colon mucosa and does not decrease after anti-TNFα therapy (FIG. 2). Colon mucosal IL7R and the 4-gene IL-7R signature are strongly and repeatedly discriminative of primary responsiveness to anti-TNFα therapy in each cohort of UC and cCD patients (FIG. 2 b,c,e) IL7R ROC AUC=98% with 95% CI: 0.92-1, 90% with 95% CI: 0.76-1, 79% with 95% CI: 0.6-0.98; 4-genes IL-7R signature ROC AUC=99% with 95% CI: 0.96-1, 95% with 95% CI: 0.86-1, 82% with 95% CI: 0.63-1. Altogether, our meta-analysis argues that the pretreatment mucosal IL-7R signaling signature and IL-7Rα expression in the colon could predict the nonresponsivess to anti-TNF therapy in both UC and cCD patients.

Analysis of the transcriptional IL7R signaling signature (20 genes previously described) revealed that the IL7R signaling signature, in particular IL7R, is already elevated in colon biopsies of primary UC non-responder patients before initiation of anti-TNF therapy (FIG. 3 a,b,c). A lasso (least absolute shrinkage and selection operator) regression analysis identified a combination of 10 genes (IL7R, IL2RG, JAK1, PIK3CA, LCK, BCL2, EP300, NMI, CRLF2 and TSLP) within this IL7R signaling signature able to discriminate anti-TNF non-responders from responders. Pretreatment expression of IL7R or the 10-genes IL7R-restricted signature strongly discriminates primary nonresponsiveness to anti-TNF therapy in this meta-analysis (IL7R ROC AUC=84%, 10-genes IL7R signature ROC AUC=94%) (FIG. 3 d). The absence of IL7R expression in the signature decreased correlation with anti-TNF response (AUC=82%). These data suggest that the entire pathway is associated with the non-response to anti-TNF, from IL7 receptor to transcriptionally regulated proteins (i.e. ITGA4) through major key signaling (JAK/STAT, PI3K) components. Analysis within each cohort independently, showed that pretreatment individual baseline IL7R expression is significantly increased in UC but also in cCD non-responder colon mucosa and does not decrease after anti-TNF therapy (Data not shown). Colon mucosal IL7R and the 10-gene IL7R signature are strongly and repeatedly discriminative of primary responsiveness to anti-TNF therapy in four different cohorts of UC and cCD patients (10-genes IL7R signature ROC AUC=87%, 95%, 95%, 98%). Finally, colon mucosa gene expression analysis of a single recent cohort of UC patients treated with anti-α4β7 (vedolizumab) therapy confirmed also that IL7R signaling signature is altered and IL7R is differentially expressed between responders and non-responders at early (week 6) or late (week 52) time-points post-treatment (FIG. 4). Altogether, our meta-analysis argues that the pretreatment mucosal IL7R signaling signature and IL7R expression in the colon is strongly associated with the nonresponsivess to anti-TNF, presumably also with anti-α4β7 therapy, in UC and cCD patients (Table 1) and associated with a local deficit in Tregs.

Table 1 IL7R expression significance in active IBD mucosa versus healthy controls after treatment with immunosuppression and/or corticosteroids, or before therapy with anti-TNF or anti-α4β7 between responders and non-responders.

| | Biopsy | Disease | Data type | Origin of samples | Treatment | Control (n) | IBD (n) Active | IBD (n) Inactive | p-value | ROC (AUC %) |
|---|---|---|---|---|---|---|---|---|---|---|
| After treatment | colon | Ulcerative colitis | Microarray (GSE38713) | Spain | Immunosuppressors | 13 | 15 | 8 | $1.0 \times 10^{-7}$ | |
| | colon | Ulcerative colitis | Microarray (GSE59071) | Belgium | Immunosuppressors/anti-TNF | 11 | 74 | 23 | $5.4 \times 10^{-8}$ | |
| | colon | Crohn's | Microarray (GSE59071) | Belgium | Immunosuppressors | | 8 | | $<2 \times 10^{-4}$ | |
| | colon | Ulcerative colitis | RT-qPCR | France | Immunosuppressors/anti-TNF | 24 | 21 | | $<1 \times 10^{-4}$ | |
| | colon | Crohn's | RT-qPCR | France | Immunosuppressors/anti-TNF | | 20 | | $2.4 \times 10^{-3}$ | |
| | ileal | Ulcerative colitis | RNA-SEQ (GSE57945) | North America | untreated - newly diagnosed | 42 | 38 | | n.s. | |
| | ileal | Crohn's | RNA-SEQ (GSE57945) | North America | untreated - newly diagnosed | | 174 | | n.s. | |

| | Biopsy | Disease | Data type | Origin of samples | Treatment | Control | anti-TNF/anti-α4β7 Responders | anti-TNF/anti-α4β7 Non-responders | p-value | ROC (AUC %) |
|---|---|---|---|---|---|---|---|---|---|---|
| | colon | Ulcerative colitis | Microarray (GSE16879) | Belgium | anti-TNF | 6 | 8 | 16 | $7.1 \times 10^{-3}$ | |
| | colon | Crohn's | Microarray (GSE16879) | Belgium | anti-TNF | | 12 | 7 | $1.0 \times 10^{-4}$ | |
| | colon | Ulcerative colitis | Microarray (GSE23597) | Phase III ACT1 | anti-TNF | | 25 | 6 | $3 \times 10^{-4}$ | |

-continued

| | | | | | | | | | |
|---|---|---|---|---|---|---|---|---|---|
| | colon | Ulcerative colitis | Microarray (GSE73661) | Belgium | anti-TNF | 12 | 8 | 15 | 6.7 × 10⁻³ | |
| | colon | Ulcerative colitis | Microarray (GSE73661) | Phase III GEMINI | anti-α4β7 | | 9 | 32 | 9.0 × 10⁻⁴ | |
| Before treatment | colon | Ulcerative colitis | Microarray (GSE12251) | Phase III ACT1 | anti-TNF | | 12 | 10 | 1.0 × 10⁻² | 0.79 |
| | colon | Ulcerative colitis | Microarray (GSE16879) | Belgium | anti-TNF | 6 | 8 | 16 | 2.5 × 10⁻⁴ | 0.90 |
| | colon | Crohn's | Microarray (GSE16879) | Belgium | anti-TNF | | 12 | 7 | 1.4 × 10⁻⁶ | 0.98 |
| | colon | Ulcerative colitis | Microarray (GSE73661) | Belgium | anti-TNF | 12 | 8 | 15 | 1.3 × 10⁻² | 0.82 |
| | colon | Ulcerative colitis | Microarray (GSE73661) | Phase III GEMINI | anti-α4β7 | | 9 | 32 | n.s. | 0.69 |
| | colon | Ulcerative colitis | Microarray (GSE23597) | Phase III ACT1 | anti-TNF | | 25 | 6 | n.s. | |
| | ileal | Crohn's | Microarray (GSE16879) | Belgium | anti-TNF | 6 | 8 | 10 | n.s. | |
| | | | Total (n) | | | | 114 | 559 (incl. 165 anti-TNF treated patients) | | |

Characterization of Mucosal IL7/IL7R Expression

Our study revealed that key players of the IL7R signaling signature and notably individual expression of IL7R at baseline are reproducibly and strongly associated with a considerable risk of resistance to anti-TNF in 3 different cohorts of UC and 1 cohort of CD. IL7R pathway association with resistance to anti-α4β7 therapy has been also observed. Our data also highlight potentially useful biomarkers of colon inflammation capable of identifying patients who will achieve full remission from those who will be completely nonresponsive following therapy.

Our results indicate that the IL7R pathway is locally dysregulated in the colon of severe IBD patients and may contribute to the maintenance of chronic inflammation. More importantly, our study identified that a high colonic IL7R signaling gene signature, particularly IL7R, is reproducibly and strongly associated with the absence of response to anti-TNF and also to anti-α4β7 therapies both in UC and Crohn's disease patients before initiation of the therapy, constituting potentially a new predictive biomarker to identify these refractory patients.

Discussion

Since IBD is characterized by chronic inflammation, most targeted therapies are directed to dampen downstream effectors of dysregulated immune responses (i.e. inflammatory cytokines). However, these strategies are not particularly effective in a substantial proportion of patients and significant rates of acquired resistance are observed.

Excepting a meta-analysis reporting 29 additional UC risk loci including the IL7R gene[37], only one study in man has reported an association between the IL-7 pathway and severe IBD, whereby the transcriptional profile of circulating T cells correlated with the clinical course in UC and CD[38]. Our analysis of 6 transcriptional data sets of mucosal biopsies from UC and CD patients, and cross-validation with local cohorts by RT-qPCR quantification, revealed that the IL-7R signaling signature is reproducibly and significantly enriched in colon mucosa of active diseases and clearly discriminates the disease status from inactive states or non-IBD controls. Furthermore, several components of the entire pathway were found to be reproducibly associated and over-expressed or for some of the genes under-expressed, suggesting a potential biologically active pathway specifically located in diseased tissues. Our study revealed that key players of the IL-7R signaling signature and notably individual expression of IL7R at baseline are reproducibly and strongly correlated with a considerable risk of resistance to anti-TNF in three different cohorts. In an additional cohort[41], the IL-7R signature was elevated in non-responder patients after anti-TNFα therapy, IL7R was significantly associated with non-response to anti-TNF treatment Material and Methods Analysis of Transcriptomic Data Gene expression values for the twenty genes of interest were obtained from the Gene Expression Omnibus database (http://www.ncbi.nlm.nih.gov/geo/): GSE38713[39] and GSE59071[40] for colon biopsies from UC patients after treatment with immunosuppressants and/or corticosteroids; GSE57945[42] for ileal biopsies from pediatric healthy controls and patients with newly diagnosed and untreated ileal CD, colonic CD, or UC; GSE16879[44] for colon biopsies from UC patients as well as colon and ileal biopsies from CD patients before and 4-6 weeks after treatment with anti-TNF (infliximab), GSE12251[43] for colon biopsies of UC patients before anti-TNF (infliximab) therapy, and GSE23597[41] for colon biopsies from UC patients before and 8 weeks and 30 weeks after anti-TNF (infliximab) therapy. and GSE73661[46] for colon biopsies from UC patients before and 4-6 weeks after treatment with anti-TNF (infliximab) as well as UC patients before and 6 weeks and 52 weeks after treatment with anti-α4β7 (vedolizumab). Patients characteristics as well as criteria and definition for determining primary responsiveness to anti-TNF or anti-α4β7 therapy are described in supplementary methods. Briefly, patients with active IBD refractory to corticosteroids and/or immunosuppression underwent biopsies collection within a week before anti-TNF or anti-α4β7 therapy and at early (week 4-8) or late (week 30 or 52) timepoints after the first infusion. In all cohorts, excepting GSE23597[42], anti-TNF or anti-α4β7 response was defined by complete histological and endoscopic healing. In GSE23597[42], anti-TNF response was defined by a decrease from baseline of the total MAYO score of at least three points and 30% with an accompanying decrease of the bleeding sub-score of at least one point and an absolute bleeding sub-score of 0 or 1. This cohort of UC patients treated with anti-TNF was not included in our meta-analysis.

Gene Expression Analysis

Analyses were performed using R software version 3.3.2. Briefly, normalized collected gene expression from microarray datasets were log 2 transformed, the mean of probes targeting the same gene were calculated and the log FPKM values were collected from RNA sequencing studies. In order to analyze anti-TNFα treatment responsiveness before administration, two datasets were merged together after standardization (median centered and scaled) according to the group of colon biopsies from UC and anti-TNFα responders in each dataset[43,44]. Identification of differential genes was performed with a modified t-statistic with Bayesian adjustment and Benjamini and Hochberg false discovery rate correction using the limma[45] package in R. Genes with adjusted p-values<5% were considered as differentially expressed. From the differential genes, multivariate logistic regression between anti-TNFα responders and non-responders was performed on the meta-dataset to select genes significantly (p-values<5%) associated with anti-TNFα response. The resulting equation of this logistic regression was then used on individual datasets. Principal component analysis, clustering and ROC curves were performed in R using ade4 and adegraphics, heatmap3 and pROC packages respectively[46,47].

In order to complete the previous analyzis of anti-TNF treatment responsiveness before administration, three datasets(44-46), all from Affymetrix U133 Plus 2.0 arrays, were merged together after RMA normalization and Combat batch correction(49). Identification of differential genes according to anti-TNF response was performed with a moderated t-statistic with Bayesian adjustment and Benjamini and Hochberg false discovery rate correction using the limma(50) package in R. Genes with $\log_2$ fold change>1 and adjusted p-values<5% were considered as differentially expressed. To identify the minimal combination of genes able to discriminate anti-TNF responders from non-responders, lasso (least absolute shrinkage and selection operator) regression analysis was performed from the 20 genes of interest (R package glmnet). Relative estimation of cell abundances using gene expression data was performed through the CIBERSORT online tool(48). IL7-R pathway enrichment was assessed using the gene set enrichment analysis (GSEA(78)) software (1,000 permutations) on the meta-dataset. Principal component analysis, clustering and ROC curves were performed in R using ade4 and adegraphics, heatmap3 or pheatmap and pROC packages respectively (51, 52).

REFERENCES

1. Khor, B., Gardet, A. & Xavier, R. J. Genetics and pathogenesis of inflammatory bowel disease. *Nature* 474, 307-317 (2011).
2. Abraham, C. & Cho, J. H. Inflammatory Bowel Disease. *New England Journal of Medicine* 361, 2066-2078 (2009).
3. Danese, S. & Fiocchi, C. Ulcerative colitis. *N. Engl. J. Med.* 365, 1713-1725 (2011).
4. Baumgart, D. C. & Sandborn, W. J. Crohn's disease. *Lancet* 380, 1590-1605 (2012).
5. Ungaro, R., Mehandru, S., Allen, P. B., Peyrin-Biroulet, L. & Colombel, J.-F. Ulcerative colitis. *Lancet* 389, 1756-1770 (2017).
6. Torres, J., Mehandru, S., Colombel, J.-F. & Peyrin-Biroulet, L. Crohn's disease. *Lancet* 389, 1741-1755 (2017).
7. Allez, M. et al. Report of the ECCO pathogenesis workshop on anti-TNF therapy failures in inflammatory bowel diseases: definitions, frequency and pharmacological aspects. *J Crohns Colitis* 4, 355-366 (2010).
8. Adams, D. H. & Eksteen, B. Aberrant homing of mucosal T cells and extra-intestinal manifestations of inflammatory bowel disease. *Nat. Rev. Immunol.* 6, 244-251 (2006).
9. Agace, W. W. Tissue-tropic effector T cells: generation and targeting opportunities. *Nat. Rev. Immunol.* 6, 682-692 (2006).
10. Feagan, B. G. et al. Vedolizumab as Induction and Maintenance Therapy for Ulcerative Colitis. *New England Journal of Medicine* 369, 699-710 (2013).
11. Sandborn, W. J. et al. Vedolizumab as Induction and Maintenance Therapy for Crohn's Disease. *New England Journal of Medicine* 369, 711-721 (2013).
12. Mackall, C. L., Fry, T. J. & Gress, R. E. Harnessing the biology of IL-7 for therapeutic application. *Nat. Rev. Immunol.* 11, 330-342 (2011).
13. Mazzucchelli, R. & Durum, S. K. Interleukin-7 receptor expression: intelligent design. *Nat. Rev. Immunol.* 7, 144-154 (2007).
14. Liu, W. et al. CD127 expression inversely correlates with FoxP3 and suppressive function of human CD4+×T reg cells. *J. Exp. Med* 203, 1701-1711 (2006).
15. Seddiki, N. et al. Expression of interleukin (IL)-2 and IL-7 receptors discriminates between human regulatory and activated T cells. *J. Exp. Med.* 203, 1693-1700 (2006).
16. Michel, L. et al. Patients with relapsing-remitting multiple sclerosis have normal Treg function when cells expressing IL-7 receptor alpha-chain are excluded from the analysis. *J. Clin. Invest.* 118, 3411-3419 (2008).
17. Rochman, Y., Spolski, R. & Leonard, W. J. New insights into the regulation of T cells by gamma(c) family cytokines. *Nat. Rev. Immunol.* 9, 480-490 (2009).
18. Carrette, F. & Surh, C. D. IL-7 signaling and CD127 receptor regulation in the control of T cell homeostasis. *Semin. Immunol.* 24, 209-217 (2012).
19. Dooms, H. Interleukin-7: Fuel for the autoimmune attack. *J. Autoimmun.* 45, 40-48 (2013).
20. Mai, H.-L. et al. IL-7 receptor blockade following T cell depletion promotes long-term allograft survival. *J. Clin. Invest.* 124, 1723-1733 (2014).
21. Shalapour, S. et al. Commensal microflora and interferon-gamma promote steady-state interleukin-7 production in vivo. *Eur. J. Immunol.* 40, 2391-2400 (2010).
22. Shalapour, S. et al. Interleukin-7 links T lymphocyte and intestinal epithelial cell homeostasis. *PLoS ONE* 7, e31939 (2012).
23. Watanabe, M. et al. Interleukin 7 transgenic mice develop chronic colitis with decreased interleukin 7 protein accumulation in the colonic mucosa. *J. Exp. Med.* 187, 389-402 (1998).
24. Yamazaki, M. et al. Mucosal T cells expressing high levels of IL-7 receptor are potential targets for treatment of chronic colitis. *J. Immunol.* 171, 1556-1563 (2003).
25. Okada, E. et al. IL-7 exacerbates chronic colitis with expansion of memory IL-7Rhigh CD4+ mucosal T cells in mice. *Am. J. Physiol. Gastrointest. Liver Physiol.* 288, G745-754 (2005).
26. Totsuka, T. et al. IL-7 Is essential for the development and the persistence of chronic colitis. *J. Immunol.* 178, 4737-4748 (2007).
27. Shinohara, T. et al. Upregulated IL-7 receptor α expression on colitogenic memory CD4+ T cells may participate in the development and persistence of chronic colitis. *J. Immunol.* 186, 2623-2632 (2011).
28. Buonocore, S. et al. Innate lymphoid cells drive interleukin-23-dependent innate intestinal pathology. *Nature* 464, 1371-1375 (2010).
29. Bemink, J. H. et al. Human type 1 innate lymphoid cells accumulate in inflamed mucosal tissues. *Nat Immunol* 14, 221-229 (2013).

30. Goldberg, R., Prescott, N., Lord, G. M., MacDonald, T. T. & Powell, N. The unusual suspects—innate lymphoid cells as novel therapeutic targets in IBD. *Nat Rev Gastroenterol Hepatol* 12, 271-283 (2015).
31. Powell, N. et al. The transcription factor T-bet regulates intestinal inflammation mediated by interleukin-7 receptor+ innate lymphoid cells. *Immunity* 37, 674-684 (2012).
32. Willis, C. R. et al. Interleukin-7 receptor blockade suppresses adaptive and innate inflammatory responses in experimental colitis. *J Inflamm (Lond)* 9, 39 (2012).
33. Neurath, M. F. Cytokines in inflammatory bowel disease. *Nat Rev Immunol* 14, 329-342 (2014).
34. MacDonald, T. T., Biancheri, P., Sarra, M. & Monteleone, G. What's the next best cytokine target in IBD? *Inflamm Bowel Dis* 18, 2180-2189 (2012).
35. de Souza, H. S. P. & Fiocchi, C. Immunopathogenesis of IBD: current state of the art. *Nat Rev Gastroenterol Hepatol* 13, 13-27 (2016).
36. Watanabe, M. et al. Interleukin 7 is produced by human intestinal epithelial cells and regulates the proliferation of intestinal mucosal lymphocytes. *J. Clin. Invest.* 95, 2945-2953 (1995).
37. Anderson, C. A. et al. Meta-analysis identifies 29 additional ulcerative colitis risk loci, increasing the number of confirmed associations to 47. *Nat. Genet.* 43, 246-252 (2011).
38. Lee, J. C. et al. Gene expression profiling of CD8+ T cells predicts prognosis in patients with Crohn disease and ulcerative colitis. *J. Clin. Invest.* 121, 4170-4179 (2011).
39. Planell, N. et al. Transcriptional analysis of the intestinal mucosa of patients with ulcerative colitis in remission reveals lasting epithelial cell alterations. *Gut* 62, 967-976 (2013).
40. Vanhove, W. et al. Strong Upregulation of AIM2 and IFI16 Inflammasomes in the Mucosa of Patients with Active Inflammatory Bowel Disease. *Inflamm. Bowel Dis.* 21, 2673-2682 (2015).
41. Toedter, G. et al. Gene expression profiling and response signatures associated with differential responses to infliximab treatment in ulcerative colitis. *Am. J. Gastroenterol.* 106, 1272-1280 (2011).
42. Haberman, Y. et al. Pediatric Crohn disease patients exhibit specific ileal transcriptome and microbiome signature. *J. Clin. Invest.* 124, 3617-3633 (2014).
43. Arijs, I. et al. Mucosal gene signatures to predict response to infliximab in patients with ulcerative colitis. *Gut* 58, 1612-1619 (2009).
44. Arijs, I. et al. Mucosal gene expression of antimicrobial peptides in inflammatory bowel disease before and after first infliximab treatment. *PLoS ONE* 4, e7984 (2009).
45. Smyth, G. K. Linear models and empirical bayes methods for assessing differential expression in microarray experiments. *Stat Appl Genet Mol Biol* 3, Article3 (2004).
46. Robin, X. et al. pROC: an open-source package for R and S+ to analyze and compare ROC curves. *BMC Bioinformatics* 12, 77 (2011).
47. The ade4 Package: Implementing the Duality Diagram for Ecologists|Dray|Journal of Statistical Software. doi: 10.18637/jss.v022.i04
48. Newman A M et al. Robust enumeration of cell subsets from tissue expression profiles. *Nat. Methods* 2015; 12(5):453-457.
49. Johnson W E, Li C, Rabinovic A. Adjusting batch effects in microarray expression data using empirical Bayes methods. *Biostatistics* 2007; 8(1): 118-127.
50. Smyth G K. Linear models and empirical bayes methods for assessing differential expression in microarray experiments. *Stat Appl Genet Mol Biol* 2004; 3:Article3.
51. Robin X et al. pROC: an open-source package for R and S+ to analyze and compare ROC curves. *BMC Bioinformatics* 2011; 12:77.
52. The ade4 Package: Implementing the Duality Diagram for Ecologists|Dray|Journal of Statistical Software [Internet] doi:10.18637/jss.v022.i04

The invention claimed is:

1. A method of in vitro assessing the response status of a human patient for treatment of inflammatory bowel disease (IBD) with an anti-TNFalpha agent and/or with an anti $\alpha 4\beta 7$ agent, wherein the method comprises the steps of:
 (a) obtaining a colon mucosal sample from said human patient, and in said sample detecting a sample expression profile of transcripts of a set of genes comprising the IL7R, STAT5A, JAK1 and JAK3 genes;
 (b) comparing the detected sample expression profile to a reference expression profile of transcripts of a set of genes comprising the ILR7, STAT5A, JAK1 and JAK3 genes, wherein the expression reference profile is obtained from colon biopsies of non-IBD human control subjects;
 (c) detecting:
  expression of the set of genes in the sample profile that is overexpressed as compared to the expression of the set of genes in the reference expression profile, and predicting that the patient will be non-responsive to treatment with an anti-TNFalpha agent and/or with an anti-$\alpha 4\beta 7$ agent; or
  expression of the set of genes in the sample profile that is not overexpressed as compared to the expression of the set of genes in the reference expression profile, and predicting that the patient will be responsive to treatment with an anti-TNFalpha agent and/or with an anti-$\alpha 4\beta 7$ agent; and
 (d) administering to the subject a treatment for IBD, wherein: a predicted non-responsive patient is treated with anti-inflammatory agents, steroids, and/or immunosuppressive drugs; or a predicted responsive patient is treated with an anti-TNFalpha agent and/or with an anti-$\alpha 4\beta 7$ agent.

2. The method of claim 1, wherein the set of genes in the sample profile and the reference profile further comprises the FYN, CREBBP, PIK3CG, STAT5B, ITGA4, PIK3CA, NMI and CRLF2 genes.

3. The method of claim 1, wherein the IBD is ulcerative colitis, Crohn's disease, pediatric Crohn's disease, pediatric ulcerative colitis.

4. A method of in vitro assessing the response status of a human patient for treatment of inflammatory bowel disease (IBD) with an anti-TNFalpha agent and/or with an anti-$\alpha 4\beta 7$ agent, wherein the method comprises the steps of:
 (a) obtaining a colon mucosal sample from said human patient, and in said sample detecting a sample expression profile of transcripts of a set of genes comprising the ILR7, JAK1, IL2RG, PIK3CA, NMI, CRLF2, LCK, BCL2, EP300 and TSLP genes;
 (b) comparing the detected sample expression profile to a reference expression profile of transcripts of a set of genes comprising the ILR7, JAK1, IL2RG, PIK3CA, NMI, CRLF2, LCK, BCL2, EP300 and TSLP genes, wherein the expression reference profile is obtained from colon biopsies of non-IBD human control subjects;

(c) detecting expression of the set of genes in the sample profile that is overexpressed as compared to the expression of the set of genes in the reference expression profile, and predicting that the patient will be non-responsive to treatment with an anti-TNFalpha agent and/or with an anti-α4β7 agent; and (d) administering to the subject a treatment for IBD, wherein the predicted non-responsive patient is treated with anti-inflammatory agents, steroids, and/or immunosuppressive drugs.

5. The method of claim 1, wherein the set of genes in the sample profile and the reference profile further comprises at least one gene from the group consisting of the IL2RG, PIK3CA, NMI, CRLF2, LCK, BCL2, EP300 and TSLP genes.

6. The method according to claim 1, wherein the patient has received anti-TNFalpha treatment prior to implementation of the method.

7. The method according to claim 1, wherein the patient has not received anti-TNFalpha treatment prior to implementation of the method.

8. The method of claim 1, wherein the step (b) of comparing the sample expression profile to a reference expression profile encompasses quantitative comparison of the expression profiles.

9. The method according to claim 1, wherein detecting the sample expression profile comprises a step of detecting mRNA, or a step of detecting DNA obtained from reverse transcription of mRNA.

* * * * *